(12) United States Patent  (10) Patent No.: US 8,733,719 B2
Gaal et al.  (45) Date of Patent: May 27, 2014

(54) METHOD AND APPARATUS FOR USE IN MANAGEMENT OF MEDICAL INTRAVENOUS POLE ASSEMBLIES

(75) Inventors: Adam C. Gaal, Camillus, NY (US); Bradford J. Morse, Syracuse, NY (US)

(73) Assignee: Wildcard Enterprises LLC, Syracuse, NY (US)

( * ) Notice: Subject to any disclaimer, the term of this patent is extended or adjusted under 35 U.S.C. 154(b) by 0 days.

(21) Appl. No.: 12/945,357

(22) Filed: Nov. 12, 2010

(65) Prior Publication Data

US 2012/0119045 A1  May 17, 2012

(51) Int. Cl.
*F16B 1/00*  (2006.01)

(52) U.S. Cl.
USPC ............... 248/218.4; 248/229.26; 280/292; 294/15

(58) Field of Classification Search
USPC ........... 248/512, 513, 218.4, 219.1, 219.3, 248/122.1, 231.85, 113; 16/422; 280/304.1, 280/204, 493, 47.35, 292, 33.991–33.992; 297/243; 24/457; 211/89.01, 68, 65; 294/87.1, 15, 143, 159, 162–163
See application file for complete search history.

(56) References Cited

U.S. PATENT DOCUMENTS

| 164,088 | A | | 6/1875 | Hunteb | |
|---|---|---|---|---|---|
| 198,714 | A | * | 12/1877 | Uibel | 248/113 |
| 712,898 | A | * | 11/1902 | Barney | 297/248 |
| 1,117,491 | A | * | 11/1914 | Hornung | 211/63 |
| 1,911,781 | A | * | 5/1933 | Wolfe, Jr. | 248/113 |
| 1,925,767 | A | * | 9/1933 | Mallory | 248/113 |
| 2,696,963 | A | | 12/1954 | Shepherd | |
| 3,709,372 | A | | 1/1973 | Alexander | |
| 3,709,556 | A | | 1/1973 | Allard | |
| 3,872,945 | A | | 3/1975 | Hickman | |
| 4,190,224 | A | | 2/1980 | LeBlanc et al. | |
| 4,225,104 | A | * | 9/1980 | Larson | 248/125.8 |
| 4,332,378 | A | | 6/1982 | Pryor | |
| 4,489,454 | A | | 12/1984 | Thompson | |
| 4,511,157 | A | | 4/1985 | Wilt | |
| 4,511,158 | A | | 4/1985 | Varga et al. | |
| 4,547,092 | A | | 10/1985 | Vetter et al. | |
| 4,572,536 | A | | 2/1986 | Doughty | |
| 4,600,209 | A | | 7/1986 | Kerr | |

(Continued)

FOREIGN PATENT DOCUMENTS

WO  2012065053 A3  5/2012

OTHER PUBLICATIONS

Henshaw, Guidelines for Nursing Homes, OSHA 3182-3R, Mar. 2009, U.S. Department of Labor, pp. 1-44.

(Continued)

*Primary Examiner* — Terrell Mckinnon
*Assistant Examiner* — Ingrid M Weinhold
(74) *Attorney, Agent, or Firm* — Heslin Rothenberg Farley & Mesiti P.C.; George S. Blasiak

(57) ABSTRACT

There is set forth herein a method and apparatus for use in management of medical intravenous pole assemblies. In one embodiment, an apparatus can be provided that is adapted for connection to a plurality of intravenous pole assemblies. The apparatus can be connected to a group of intravenous pole assemblies to define a group of connected intravenous pole assemblies. A force can be imparted to the group of connected intravenous pole assemblies for transport of the group of intravenous pole assemblies.

27 Claims, 11 Drawing Sheets

(56) References Cited

U.S. PATENT DOCUMENTS

| | | | |
|---|---|---|---|
| D287,055 S | 12/1986 | Fick et al. | |
| 4,676,687 A | 6/1987 | Koffler | |
| 4,725,027 A | 2/1988 | Behanich | |
| 4,729,576 A | 3/1988 | Roach | |
| 4,767,131 A | 8/1988 | Springer et al. | |
| 4,795,122 A | 1/1989 | Petre | |
| 4,886,237 A | 12/1989 | Dennis | |
| 4,905,944 A | 3/1990 | Jost et al. | |
| 4,945,592 A | 8/1990 | Sims et al. | |
| 4,969,768 A * | 11/1990 | Young | 403/97 |
| 5,083,807 A | 1/1992 | Bobb et al. | |
| 5,094,418 A | 3/1992 | McBarnes et al. | |
| 5,112,074 A | 5/1992 | Smith | |
| 5,117,521 A | 6/1992 | Foster et al. | |
| 5,118,127 A | 6/1992 | Partington | |
| 5,135,191 A | 8/1992 | Schmuhl | |
| 5,149,036 A | 9/1992 | Sheehan | |
| 5,169,106 A | 12/1992 | Rasmussen | |
| 5,172,927 A | 12/1992 | Bobb et al. | |
| 5,217,240 A * | 6/1993 | Gardenhour et al. | 280/282 |
| 5,219,139 A | 6/1993 | Hertzler et al. | |
| 5,236,213 A | 8/1993 | Trickett | |
| D346,655 S * | 5/1994 | Harris | D24/128 |
| 5,319,816 A | 6/1994 | Ruehl | |
| 5,332,184 A | 7/1994 | David | |
| 5,337,992 A | 8/1994 | Pryor et al. | |
| 5,344,169 A | 9/1994 | Pryor et al. | |
| 5,355,539 A | 10/1994 | Boettger | |
| 5,358,205 A | 10/1994 | Starkey et al. | |
| 5,366,191 A | 11/1994 | Bekanich | |
| 5,400,995 A | 3/1995 | Boyd | |
| 5,407,163 A | 4/1995 | Kramer et al. | |
| 5,421,548 A | 6/1995 | Bennett | |
| 5,482,239 A * | 1/1996 | Smith | 248/229.13 |
| 5,499,721 A | 3/1996 | Hansen et al. | |
| 5,513,406 A | 5/1996 | Foster et al. | |
| 5,527,289 A | 6/1996 | Foster et al. | |
| 5,556,065 A | 9/1996 | Wadley | |
| 5,562,091 A | 10/1996 | Foster et al. | |
| 5,577,279 A | 11/1996 | Foster et al. | |
| 5,588,166 A | 12/1996 | Burnett | |
| 5,647,491 A | 7/1997 | Foster et al. | |
| 5,680,661 A | 10/1997 | Foster et al. | |
| D386,076 S | 11/1997 | Moore | |
| 5,699,988 A | 12/1997 | Boettger et al. | |
| 5,704,577 A | 1/1998 | Gordon | |
| 5,725,185 A | 3/1998 | Auclair | |
| 5,774,876 A | 6/1998 | Woolley et al. | |
| 5,779,207 A | 7/1998 | Danby | |
| 5,898,961 A | 5/1999 | Ambach | |
| 5,915,715 A | 6/1999 | Ford | |
| 5,918,892 A * | 7/1999 | Aaron et al. | 280/47.38 |
| 5,923,432 A | 7/1999 | Kral | |
| 5,966,760 A | 10/1999 | Gallant et al. | |
| 5,987,670 A | 11/1999 | Sims et al. | |
| 6,073,285 A | 6/2000 | Ambach et al. | |
| 6,079,678 A | 6/2000 | Schott et al. | |
| 6,105,915 A | 8/2000 | Naman et al. | |
| 6,179,260 B1 | 1/2001 | Ohanian | |
| 6,182,662 B1 | 2/2001 | McGhee | |
| 6,273,444 B1 | 8/2001 | Power | |
| 6,286,847 B1 | 9/2001 | Perrin | |
| 6,296,261 B1 | 10/2001 | DeGoma | |
| 6,360,389 B1 | 3/2002 | Gallant et al. | |
| 6,374,436 B1 | 4/2002 | Foster et al. | |
| 6,382,576 B1 | 5/2002 | Heimbrock | |
| 6,431,794 B1 | 8/2002 | Zweber | |
| 6,464,188 B1 | 10/2002 | Donovan | |
| 6,554,235 B1 | 4/2003 | Fortier | |
| 6,601,860 B2 | 8/2003 | Potter | |
| 6,622,980 B2 | 9/2003 | Boucher et al. | |
| 6,669,224 B2 | 12/2003 | Newkirk | |
| 6,688,569 B1 | 2/2004 | Weiss | |
| 6,694,548 B2 | 2/2004 | Foster et al. | |
| 6,704,956 B2 | 3/2004 | Riley et al. | |
| 6,708,991 B1 | 3/2004 | Ortlieb | |
| 6,725,474 B2 | 4/2004 | Foster et al. | |
| 6,725,483 B2 | 4/2004 | Gallant et al. | |
| 6,769,604 B2 | 8/2004 | Ichikawa et al. | |
| 6,834,840 B1 | 12/2004 | Metz et al. | |
| 6,883,563 B2 | 4/2005 | Smith | |
| 6,885,288 B2 | 4/2005 | Pincus | |
| 6,966,086 B2 | 11/2005 | Metz et al. | |
| 6,969,031 B2 | 11/2005 | Ugent et al. | |
| 6,980,111 B2 | 12/2005 | Nolte | |
| 6,993,799 B2 | 2/2006 | Foster et al. | |
| 7,008,269 B2 | 3/2006 | Riley et al. | |
| 7,065,811 B2 | 6/2006 | Newkirk et al. | |
| 7,083,150 B2 | 8/2006 | Newkirk et al. | |
| 7,154,397 B2 | 12/2006 | Zerhusen et al. | |
| 7,216,382 B2 | 5/2007 | Newkirk et al. | |
| 7,230,521 B2 | 6/2007 | Terenna | |
| 7,254,850 B2 | 8/2007 | Newkirk et al. | |
| 7,258,310 B2 | 8/2007 | Norris | |
| 7,278,615 B2 | 10/2007 | Schubert et al. | |
| 7,300,418 B2 | 11/2007 | Zaleski | |
| 7,314,200 B2 | 1/2008 | Bally et al. | |
| 7,392,621 B2 | 7/2008 | Gallant et al. | |
| 7,533,428 B2 | 5/2009 | Yunker | |
| 7,562,883 B2 | 7/2009 | Livengood et al. | |
| 7,637,464 B2 | 12/2009 | Heimbrock et al. | |
| 7,644,458 B2 | 1/2010 | Foster et al. | |
| 7,645,258 B2 | 1/2010 | White et al. | |
| D609,550 S | 2/2010 | Wan | |
| 7,676,865 B2 | 3/2010 | Graham et al. | |
| 7,716,997 B2 | 5/2010 | Healey | |
| 7,730,565 B1 | 6/2010 | Masson | |
| 7,735,266 B2 | 6/2010 | Gallant et al. | |
| D619,264 S | 7/2010 | Livengood et al. | |
| D619,265 S | 7/2010 | Livengood et al. | |
| 7,748,672 B2 | 7/2010 | Walke | |
| 7,789,361 B2 | 9/2010 | Bally et al. | |
| 7,793,902 B2 | 9/2010 | Buchanan et al. | |
| 7,798,456 B2 | 9/2010 | Newkirk et al. | |
| 7,845,601 B1 | 12/2010 | Culpepper et al. | |
| 7,865,983 B2 | 1/2011 | Newkirk et al. | |
| 7,878,523 B1 * | 2/2011 | Ferch | 280/304.1 |
| 7,884,735 B2 | 2/2011 | Newkirk | |
| 7,896,298 B2 | 3/2011 | Meyers et al. | |
| 7,921,489 B2 | 4/2011 | Newkirk et al. | |
| 8,011,707 B1 * | 9/2011 | Summers | 294/15 |
| 8,036,925 B2 * | 10/2011 | Choubey | 705/7.12 |
| 2002/0084397 A1 | 7/2002 | Ross, Jr. | |
| 2006/0038098 A1 * | 2/2006 | Metz et al. | 248/229.1 |
| 2006/0065713 A1 * | 3/2006 | Kingery | 235/380 |
| 2007/0157385 A1 | 7/2007 | Lemire et al. | |
| 2007/0273517 A1 | 11/2007 | Govind | |
| 2007/0282181 A1 | 12/2007 | Findlay et al. | |
| 2008/0111365 A1 | 5/2008 | Kraabel | |
| 2008/0190460 A1 | 8/2008 | Berklund et al. | |
| 2009/0051546 A1 | 2/2009 | Bhavani | |
| 2009/0069637 A1 * | 3/2009 | Healey | 600/300 |
| 2009/0146027 A1 * | 6/2009 | Zitting et al. | 248/176.1 |
| 2009/0182594 A1 | 7/2009 | Choubey | |
| 2010/0007498 A1 * | 1/2010 | Jackson | 340/572.1 |
| 2010/0090004 A1 | 4/2010 | Sands et al. | |
| 2011/0037565 A1 * | 2/2011 | Skirble et al. | 340/8.1 |

OTHER PUBLICATIONS

S. Ford, Nurses Waste 'an Hour a Shift' Finding Equipment, http://www.nursingtimes.net/nurses-waste-an-hour-a-shift-finding-equipment/1987381.article, Feb. 10, 2009, 2 pages.

Nicholas Graves, Economics of Preventing Hospital Infection, Emerging Infection Diseases, vol. 10, No. 4, Apr. 2004, http://wwwnc.cdc.gov/eid/article/10/4/02-0754_article.htm, 12 pages.

Julie E. Williamson, CO MD Publishing, Optimizing Asset Management, Equipment Utilization More Essential Than Ever, Jul. 9, 2009, http://www.labx.com/article.cfm?articleid=1461, 3 pages.

Goo Sung, Core77 Case Study: Modo's IV Pole for Cardinal Health, May 2, 2009, http://www.core77.com/blog/featured_items/_core77_case_study_modos_iv_pole_for_cardinal_health_by_goo_sung_13354.asp, 14 pages.

(56) References Cited

OTHER PUBLICATIONS

Greg Thompson, Easing Infusion Confusion, Aug. 2009, http://www.24x7mag.com/issues/articles/2009-08_03.asp, 4 pages.
Guidelines for Nursing Homes, Ergonomics for the Prevention of Musculoskeletal Disorders, OSHA 3182, 2003, U.S. Department of Labor, http://www.osha.gov/ergonomics/guidelines/nursinghome/final_nh_guidelines.html, pp. 1-23.
A. L. Cohen, C. C. Gjessing, L. J. Fine, B. P. Bernard, J. D. Mcglothlin, Elements of Ergonomics Programs, US Department of Heath and Human Services, NHHS (NIOSH) Publication No. 97-117, Mar. 1997, 146 pages.
International Search Report dated May 18, 2012 for PCT/US2011/060354.
Status Report for PCT/US2011/060354 generated on Jan. 22, 2013.
May 21, 2013 Written Opinion of the International Searching Authority in PCT/US2011/060354, 8 pages.
Centicare Corporation, Product Line Catalog, http://centicare.com-index.html, dated Nov. 1, 2010 (43 pages).
Centicare Corporation, Product Line Catalog, http://centicare.com-iv_poles.html, dated Oct. 29, 2010 (2 pages).
Hardware and Tools Product Review, Broom Holder Claim Type SS28-6 by Lehigh Group Crawford products, http://www.hardwareandtools.com-invt-8849192, dated Feb. 11, 2010 (2 pages).
PR Log Free Press Release, Magic Holder Broom & Mop Organizer, http://www.prlog.org-10192851-magic-holder-broom-mop-organizer.html, dated Mar. 4, 2009 (2 pages).

* cited by examiner

METHOD AND APPARATUS FOR USE IN MANAGEMENT OF MEDICAL INTRAVENOUS POLE ASSEMBLIES

FIELD OF THE INVENTION

The invention relates to asset management in general and specifically to a method and apparatus for management of medical intravenous (IV) pole assemblies.

BACKGROUND OF INVENTION

Considerable resources are expended at hospitals and other health care facilities relative to the management of medical intravenous pole assemblies. A medical intravenous pole assembly can include a pole, a wheel equipped base, and various medical equipment (infusion pumps, feed pumps, and monitors). From time to time medical intravenous pole assemblies are transported from a hospital patient treatment location to another location. In one common practice a medical intravenous pole assembly after being used for treatment of a patient at a patient treatment location is moved to a central location, typically called Central Service (CS) or Materials Management. At the central location, an intravenous pole assembly can be disinfected and then dispatched to a next patient treatment location. Intravenous pole assemblies are continuously being moved from patient treatment locations to a central location for cleaning and maintenance and back to patient treatment locations. In order to increase equipment utilization and to increase patient throughput, attempts have been made to transport more than one medical intravenous pole assembly at a time. Specifically, workers at hospitals have attempted to move first and second medical intravenous pole assemblies simultaneously by grasping a first medical intravenous pole assembly with a first hand, grasping a second medical intravenous pole assembly with a second hand, and imparting a moving force to the two assemblies, e.g., by walking while holding the first and second assemblies.

Health care facilities expend significant resources in managing and tracking equipment assets. Intravenous pole assemblies are often unaccounted for between patient care locations and a central location. Some are later found holed up in closets or holding areas while others just go missing. Health care workers have been observed to stow away intravenous pole assemblies at undisclosed and untracked locations away from a central location out of fear that they will not be able to find one when needed. Such hoarded intravenous pole assemblies are typically not subjected to appropriate controlled cleaning procedures, as would be implemented at a central location. Because of the inability of health care facilities to manage the intravenous pole assemblies, facilities have been observed to continuously purchase additional intravenous pole assemblies including expensive pumps and monitors in numbers far in excess of that which would be necessary if a method for appropriate management of the assemblies were available.

SUMMARY OF THE INVENTION

There is set forth herein a method and apparatus for use in management of medical intravenous pole assemblies. In one embodiment, an apparatus can be provided that is adapted for connection to a plurality of intravenous pole assemblies. The apparatus can be connected to a group of intravenous pole assemblies to define a group of connected intravenous pole assemblies. A force can be imparted to the group of connected intravenous pole assemblies for transport of the group of intravenous pole assemblies.

BRIEF DESCRIPTION OF THE DRAWINGS

Features described herein can be better understood with reference to the drawings described below. The relative dimensions of features depicted in the drawings herein represent specific embodiments of apparatus, systems, and methods herein. However, it is understood that apparatus, systems, and methods herein can be provided with use of relative dimensions other than those specifically set forth in the drawings. In the drawings, like numerals are used to indicate like parts throughout the various views. In the drawings, various embodiments of apparatuses are shown having both functional and ornamental features.

DETAILED DESCRIPTION OF THE INVENTION

Figure 1:
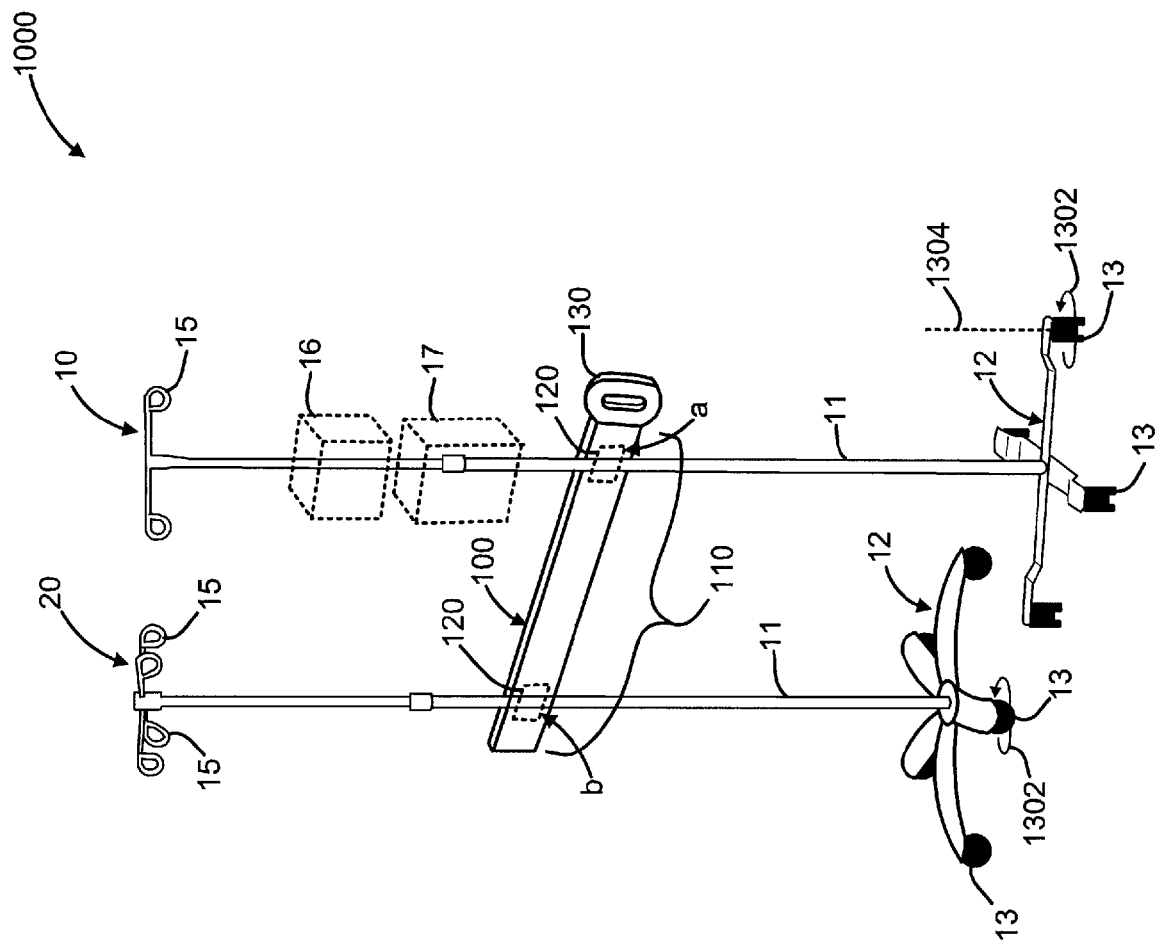
FIG. 1 is a perspective view showing a connected group of intravenous pole assemblies comprising two intravenous pole assemblies and connected utilizing the apparatus of a first type.

According to a method set forth herein a plurality of medical intravenous pole assemblies defining a group can be physically associated together to define a group of connected intravenous pole assemblies. With a group of connected intravenous pole assemblies defined, a force can be imparted to the group of connected intravenous pole assemblies to move the group. A group of connected intravenous pole assemblies can be moved, e.g., from a patient treatment location to a central location (e.g., Central Service, which can be referred to as a Central Service location) from a central location to a patient treatment location, or between patient treatment locations.

In one embodiment, there is set forth herein a method for use in management of a group of intravenous pole assemblies comprising at least first and second intravenous pole assemblies, the method comprising providing an apparatus including an arm having disposed thereon a first connector adapted for connecting to an intravenous pole assembly and a second connector adapted for connecting to an intravenous pole assembly, the arm being adapted for providing a spacing between the first connector and the second connector, connecting the first connector to the first intravenous pole assembly and connecting the second connector to the second intravenous pole assembly, whereupon there is defined by the connecting of the first connector to the first intravenous pole assembly and the connecting of the second connector to the second intravenous pole assembly a group of connected intravenous pole assemblies, and imparting a force to move the group of connected intravenous pole assemblies.

It will be understood that for performance of providing of an apparatus herein as described in connection with various methods for use in management of a group of intravenous pole assemblies, a providing can be performed without manufacture of an apparatus, e.g., by merely positioning or otherwise disposing for use an apparatus having a recited set of constituent elements. A manufacturer of an apparatus provided as part of a method set forth herein can be an entity other than the entity performing the method, or in one embodiment, a manufacturer of an apparatus provided as part of a method set forth herein can be the same entity performing the method.

In one embodiment of a method, a first medical intravenous pole assembly can be identified together with a second medical intravenous pole assembly, wherein the first medical intravenous pole assembly and a second medical intravenous pole assembly may also be identified for transport, e.g., to a central location (e.g., Central Service) where intravenous pole assemblies can be temporarily stored and subject to cleaning.

Rather than transporting the first medical intravenous pole assembly and the second medical intravenous pole assembly to the central location separately, a method as set forth herein calls for first and second medical intravenous pole assemblies to be physically associated for transport to a destination. According to a method, a first and second medical intravenous pole assembly can be physically associated to form a group of connected medical intravenous pole assemblies and then transported as a unit (a group of connected intravenous pole assemblies) to a destination location.

In one embodiment, the method can provide for maintaining a spacing between medical intravenous pole assemblies. In one embodiment, the providing of a spacing can provide a minimum spacing between first and second connected intravenous pole assemblies. In one embodiment, the spacing can be a predetermined spacing. Spacing discourages intravenous pole assemblies (which can include equipment articles such as infusion pumps) from being entangled and thereby encourages smooth movement of a group of medial intravenous pole assemblies.

In one embodiment, the method can provide for allowing pushing of group of poles for transport of a group of poles. In another embodiment, a method as set forth herein provides for allowing pulling of a group of connected medical intravenous pole assemblies. In another embodiment, a method as set forth herein allows for one or more of pushing and pulling a group of connected medical intravenous pole assemblies.

An apparatus 100 for use in a method set forth herein is shown in FIG. 1. Apparatus 100 as shown in FIG. 1 facilitates a connection between first and second medical intravenous pole assembly 10, 20.

Referring to aspects of typical intravenous pole assemblies, medical intravenous pole assemblies, e.g., assembly 10, 20 can include a pole 11 and base 12. Base 12 can include a plurality of wheels 13. There can be connected to pole 11 a hook 15. There can also be carried on an intravenous pole assembly, e.g., assembly 10, assembly 20, one or more equipment article, which, when connected to a remainder of intravenous pole assembly 10, 20 can be regarded as part of assembly 10, 20. Such equipment articles can include a fluid pump 16, e.g., an infusion pump or a feed pump, and/or a monitor 17, e.g., a heart rate monitor. Equipment articles can also include the types of devices, e.g., a medical lamp. Equipment articles, e.g., 16, 17 are typically connected to a pole 11 with use of brackets (not shown) or according to one style of intravenous pole assembly, are disposed on a shelf integrated onto intravenous pole assembly. On hook 15, there can be disposed a fluid bag, e.g., a blood bag, a nutrient bag typically subject to pumping with use of pump 16. With use of apparatus 100, a group of connected intravenous assemblies 1000 can be defined. In the use case view of FIG. 1, a group of connected intravenous pole assemblies can be regarded as including first and second medical intravenous pole assemblies 10, 20 connected with use of apparatus 100. In one aspect of a method as set forth herein in one embodiment, intravenous pole assemblies 10, 20 need not be customized for use with apparatus 100. Further, various intravenous pole assemblies that can be connected together with use of apparatus 100 need not be similarly configured. For example, intravenous pole assembly 10 can have a different configuration than intravenous pole assembly 20. In one embodiment, intravenous pole assembly 10 and intravenous pole assembly 20 can have poles and bases and/or equipment articles provided by different manufacturers. In the development of the method and apparatus set forth here it was observed that while intravenous pole assemblies are available in a variety of different shapes and sizes they do nevertheless tend to have elements in common One common element is that intravenous pole assemblies tend to include vertically extending poles. Embodiments of methods and apparatus herein utilize common elements of intravenous pole assemblies, which may be intravenous pole assemblies of different configurations by different manufacturers. For focusing disclosure on transportation aspects of intravenous pole assemblies, only intravenous pole assembly 10 of FIG. 1 is shown as having an equipment article. However, it is understood that a plurality of intravenous pole assemblies of a group of intravenous pole assemblies and in one embodiment each intravenous pole assembly of a group of intravenous pole assemblies as set forth herein can include one or more equipment article.

Referring now to further aspects of apparatus 100 as shown in FIG. 1, apparatus 100 in one embodiment can include arm 110. Arm 110 can include first connector 120 and second connector 120. First connector 120 can be disposed at a location "a" of arm 110. Second connector 120 can be disposed at a location "b" of arm 110. First connector 120 can be adapted for detachable attachment to an intravenous pole assembly and second connector 120 can be adapted for detachable attachment to an intravenous pole assembly. Apparatus 100 can include handle 130 extending from arm 110. Handle 130 can be adapted for grasping by a user. In one embodiment, handle 130 can include a feature specially adapting handle 130 for grasping. Such feature can include a closed or semi-closed perimeter shape, e.g., an open center circle or square, a curved configuration, or a material construction specifically adapting handle 130 for grasping, e.g., a resilient material construction.

For use of apparatus 100 in forming a group of connected medical intravenous pole assemblies, apparatus 100 can be associated to first and second medical intravenous pole assemblies in the following manner. As an initial step, first connector 120 at location "a" as shown in FIG. 1, can be placed into proximity with first medical intravenous pole 10 and connected to pole 11 of first medical intravenous pole assembly 10. As a second step, second connector 120 at location "b" as shown in FIG. 1 can be placed into proximity with second medical intravenous pole assembly 20 and connected to second intravenous pole assembly 20. When a group of connected intravenous pole assemblies is defined, a force, e.g., a horizontal force can be imparted to the group of connected intravenous pole assemblies to move the group of connected intravenous pole assemblies.

Figure 2:
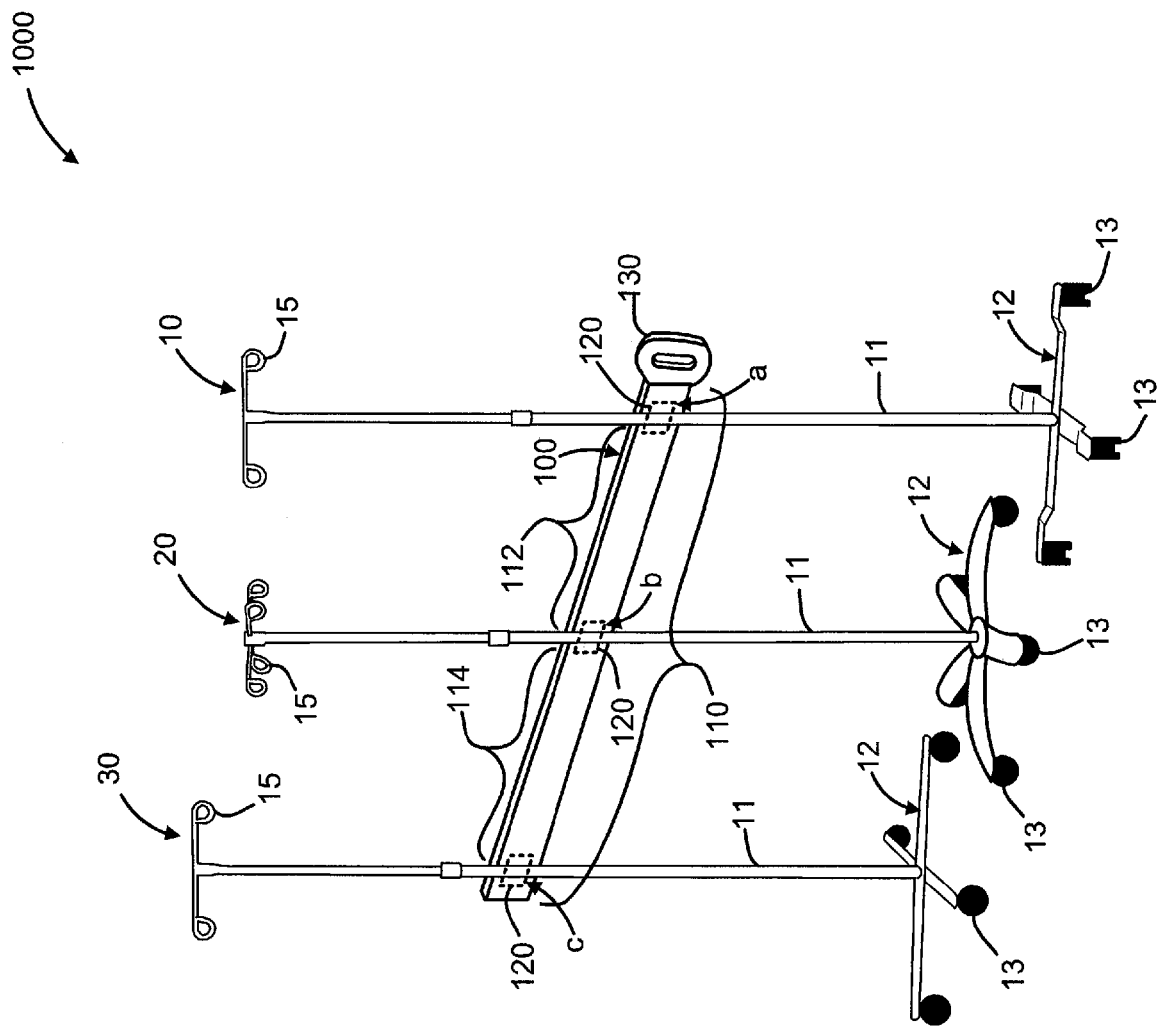
FIG. 2 is a perspective view of a group of connected intravenous pole assemblies comprising first, second and third intravenous pole assemblies that are connected together utilizing an apparatus of a second type having disposed on an arm thereon three connectors at spaced apart locations on the arm.

In one embodiment, apparatus 100 can facilitate a physical association to form a connection group of two, three, or more medical intravenous pole assemblies. Referring to FIG. 2, apparatus 100 can be configured so that arm 110 has first connector 120 at a first location, location "a," second connector 120 at a second location, location "b," and third connector 120 as a third location, location "c" of arm 110, each of the first, second and third positions being spaced apart from one another. Arm 110 in the embodiment of FIG. 2 can include a first segment 112 extending substantially between the location "a" and the location "b" and a second segment 114 extending substantially between the location "b" and the location "c". Arm 110 can be of unitary construction or in another embodiment can comprise a plurality of separate components. Segment 112 can be of unitary construction or else can comprise a plurality of segment components.

In one embodiment, arm 110 can be adapted so that arm 110 has an adjustable length. In one embodiment, apparatus 100 can be adapted so that in a first state, arm 110 has a first length defined substantially by the sum of the lengths of the first segment 112 and the second segment 114. Apparatus 100 can further be adjusted so that in a second contracted state, arm 110 can have a second contracted length defined substantially by the length of the first segment. In one example, second segment 114 can be in telescoping fitting relation with first segment 112.

Referring to FIG. 1, an apparatus 100 for use in transport of a group of intravenous pole assemblies 10, 20 comprising first intravenous pole assembly 10 and second intravenous pole assembly 20 is described.

Referring to apparatus 100 in the embodiment as shown in FIG. 1, apparatus 100 can include arm 110 and a handle 130 disposed at a proximal end of arm 110. In the embodiment of FIG. 1, arm 110 can comprise a member of unitary construction. There can be disposed on arm 110 a first connector 120 disposed at location "a" and a second connector 120 disposed at location "b."

In one aspect, arm 110 can be adapted to provide a spacing between first connector 120 at location "a" and second connector 120 at location "b." Accordingly, when connectors 120 are connected to respective intravenous pole assemblies, spacing is provided between intravenous pole assemblies to allow a connected group of intravenous pole assemblies to be moved throughout a health care facility. The spacing between the first and second connectors can be established at such distance that wheels 13 of a pair of adjacent intravenous pole assemblies do not become entangled with one another during transport of a group of intravenous pole assemblies.

Referring now to aspects of intravenous pole assemblies which can be transported with use of apparatus 100 as described herein, an intravenous pole assembly e.g., assembly 10 can comprise pole 11 extending vertically from base 12. Base 12 can include and support a plurality of wheels 13. Wheel 13 can be mounted on a base 12 in such manner to allow a 360 degree rotation of wheels 13 about a vertically extending axis 1304. Each wheel 13 of an intravenous pole assembly e.g., 10 can be similarly mounted in such manner that intravenous pole assembly 10 can be easily moved in any direction on a health care facility floor.

The second intravenous pole assembly, e.g., pole assembly 20, can be constructed similarly to intravenous pole assembly 10, but can have a different style as shown in FIG. 1. The different style can be attributable to the second intravenous pole assembly 20 having a pole 11 and base 12 being manufactured by a different manufacturer than the manufacturer of the pole 11 and base 12 of intravenous pole assembly 10.

Referring to FIG. 2 there is shown apparatus 100 for use in transport of a group of intravenous pole assemblies. Apparatus 100 as shown in FIG. 2 is of a different style of apparatus 100 as shown in FIG. 1.

Referring again to FIG. 1, apparatus 100 can be utilized in the following manner. Intravenous pole assembly 10 can be brought into proximity with connector 120 at location "a" and connector 120 can be connected to pole 11 of intravenous pole assembly 10. With the connector at location "a" connected, intravenous pole assembly 20 can be brought into proximity with the connector 120 at location "b" and the connector 120 at location "b" can be connected to pole 11 of intravenous pole assembly 20. With the connector 120 at location "a" and the connector 120 at location "b" connected with respective intravenous pole assemblies 10, 20, a group of connected intravenous pole assemblies is defined. When in a state connecting a plurality of intravenous pole assemblies, arm 110 of apparatus 100 can extend substantially horizontally and transverse to the direction of intravenous poles 11 of a group of intravenous pole assemblies. With a group of intravenous pole assemblies in a connected state, the group of intravenous pole assemblies can be moved by imparting a force to the group of connected intravenous pole assemblies.

Such force can be imparted in a generally horizontal direction, e.g., at least have a horizontal force vector component. Such force, e.g., a pushing or pulling force can be initiated, e.g., by a manual grasping by an operator, e.g., at handle 130, pole 11 of assembly 10 or of assembly 20, or at a base 12 of one or more of the intravenous pole assemblies. For configuring arm 110 to provide a spacing between connector 120 at a first location and connector 120 at a second location, arm 110 can be provided with use of material of rigid or semi-rigid construction e.g., a metal, polycarbonate, polystyrene foam (e.g., STYROFOAM by Dow Chemical Company) and the like.

There is set forth in various embodiments herein a method for transport of a group of intravenous pole assemblies comprising at least first and second intravenous pole assemblies, the method comprising providing an apparatus including an arm having disposed thereon a first connector adapted for connecting to an intravenous pole assembly and a second connector adapted for connecting to an intravenous pole assembly, the arm being adapted for providing a spacing between the first connector and the second connector; connecting the first connector to the first intravenous pole assembly and connecting the second connector to the second intravenous pole assembly, whereupon there is defined by the connecting of the first connector to the first intravenous pole assembly and the connecting of the second connector to the second intravenous pole assembly a group of connected intravenous pole assemblies; imparting a force to move the group of connected intravenous pole assemblies.

Referring to the apparatus of FIG. 2, apparatus 100 can include arm 110 and handle 130. Arm 110 in one embodiment can comprise a member of unitary construction. There can be disposed on arm 110 a connector 120 at location "a," a connector 120 at location "b," and a connector 120 at location "c." Locations "a," "b," and "c" can be spaced apart from one another. Arm 110 in the embodiment of FIG. 2 can include a first segment 112 extending between location "a" and location "b" and the second segment 112 extending between location "b" and the location "c." The apparatus 100 as shown in FIG. 2 can be utilized for transport of a group of intravenous pole assemblies comprising first, second, and third intravenous pole assemblies 10, 20 and 30. For formation of a connected group of intravenous pole assemblies, apparatus 100 can be connected to the group of intravenous pole assemblies 10, 20, and 30. For example, pole 11 of intravenous pole assembly 10 can be brought into proximity of connector at location "a," (e.g., by movement of assembly 10 or apparatus 100 or both). Connector 120 at location "a" can be connected to pole 11 intravenous pole assembly 10. Intravenous pole assembly 20 can be brought to proximity with connector 120 at location "b." Connector 120 at location "b" can be connected to pole 11 of intravenous pole assembly 20. Further, intravenous pole assembly 30 can be brought into proximity with connector 120 at location "c" and connector 120 at location "c" can be connected to pole 11 of intravenous pole assembly 30. Another ordering of connections between connectors to specific intravenous pole assemblies can be provided. With apparatus 100 connected between a group of three intravenous pole assemblies 10, 20, and 30, a group of connected intravenous pole assemblies can then be moved by impartation of a force to the connected group of intravenous pole assemblies. Such force can be initiated, e.g., by grasping, e.g., at handle 130 or at another location of the connected group of intravenous pole assemblies that is defined by the connecting of apparatus 100 to a plurality of intravenous pole assemblies.

Figure 3:
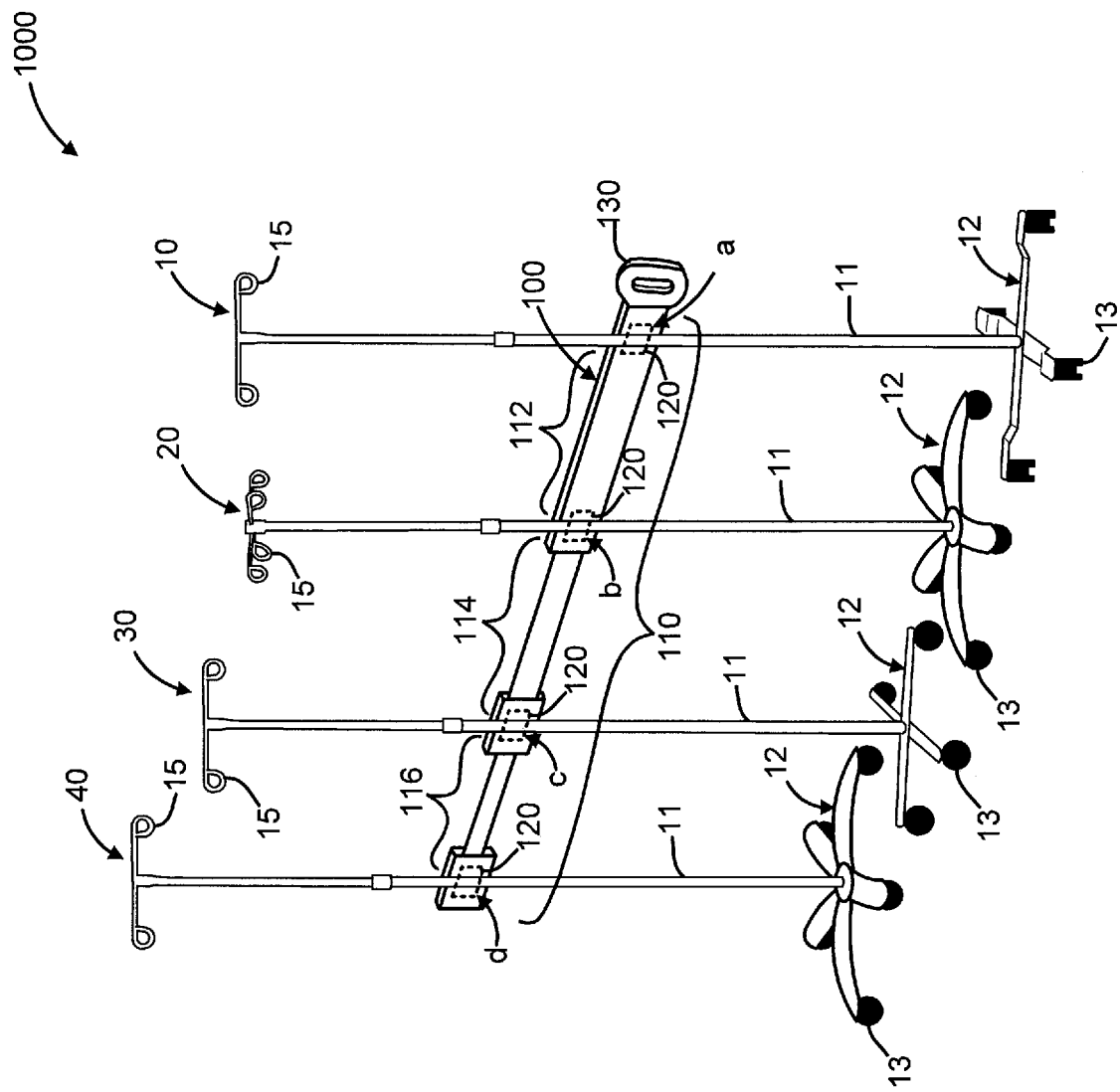
FIG. 3 is a perspective view of a group of connected intravenous pole assemblies connected together utilizing an apparatus of a third type wherein the apparatus has a plurality of connectors disposed at spaced apart locations of an extended arm thereon and wherein the arm comprises a plurality of telescoping members providing an adjustment of a length of the arm.

Referring to FIG. 3, in apparatus 100 for use in transport of a group of intravenous pole assemblies it is shown an environment where apparatus 100 is utilized for transport of a group of four intravenous pole assemblies 10, 20, 30, and 40. As indicated, intravenous pole assemblies 10, 20, 30, and 40 can be of varying style. Apparatus 100 in the embodiment of FIG. 3 can include arm 110 and handle 130. A plurality of spaced apart connectors 120 can be disposed on arm 110 at spaced apart locations "a," "b," "c," and "d" as shown in FIG. 3.

Referring to the embodiment shown in FIG. 3, arm 110 can include a first segment 112 extending between a first location "a" and a second location "b." The second segment 114 extending between a second location "b" and a third location "c" and a third segment 116 extending between location "c" and location "d."

In the particular embodiment of FIG. 3, arm 110 is not provided by a member of unitary construction but rather can be provided by a plurality of inter-fitting members.

Figure 4:
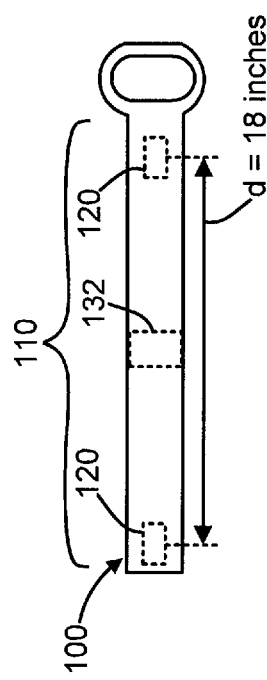
FIG. 4 is a front view of an apparatus in use for connecting a plurality of intravenous pole assemblies.

In a particular embodiment of FIG. 3, arm 110 is shown as being provided by a plurality of telescoping members. Referring to the embodiment of FIG. 3, first segment 112 can be provided by a hollowed telescoping member which telescopically receives the second member that defines a second segment 114. The member defining second segment 114 in turn can be hollowed for telescopic receipt of a third member defining segment 116. Referring to the telescopic member embodiment of FIG. 3, such embodiment of apparatus 100, a configuration of apparatus 100 can be reconfigurable between compacted states and expanded states as can be shown in FIG. 3 (expanded state). The compact and expanded states can alternatively be referred to as compacted and expanded configuration. A configuration of apparatus 100 can be changed to an expanded configuration for connection of apparatus 100 to a plurality of intravenous pole assemblies including more than two intravenous pole assemblies. When apparatus 100 is not in use at a patient treatment location, i.e., is being temporarily stored at a central location (e.g., Central Service) or at a health care worker work station, apparatus 100 can be reconfigured into a compacted configuration for a reduction of a volume consumed by apparatus 100. Telescoping member embodiment of FIG. 3 allows for connection of apparatus 100 to three or more intravenous pole assemblies while allowing for small sized storage configuration. In another embodiment, as indicated in the view of FIG. 4, apparatus 100 can be made reconfigurable between compacted and expanded states with use of an optional hinge 132, shown in dashed form as shown in FIG. 4 allowing 180 degree hinging of arm 110 about hinge. With hinge 132, arm 110 is movable between an expanded state in which arm 110 has a length, l, or approximately l=d and a contracted state in which arm 110 has a length l, of approximately l=½ d.

In the embodiment of FIG. 3, apparatus 100 includes three telescoping members; namely, a first telescoping member defining first segment 112, a second telescoping member defining segment 114, and a third telescoping member defining segment 116. However, it would be understood that in another embodiment apparatus 100 can be provided to include fewer telescoping members, e.g., two telescoping members or zero telescoping members. In other embodiments apparatus 100 can be configured to include more than three telescoping members, e.g., four or more telescoping members.

Referring to FIG. 4, FIG. 4 is a front view of an exemplary apparatus 100 for use in transporting a plurality of intravenous pole assemblies is described. The embodiment of FIG. 4 illustrates an exemplary spacing between a pair of connectors 120 of an arm 110. In the embodiment of FIG. 4 the pair of connectors 120 are center spaced to a distance of 18 inches or 45.72 centimeters. Such spacing can be determined based on base dimensions of a variety of commonly available different styled intravenous pole assemblies. With the considered sample of intravenous pole assemblies it can be expected that the performance of apparatus 100 will not be substantially affected if a spacing is reduced by twenty percent. Different spacings for connectors can be appropriate for different samples of intravenous pole assemblies. The spacing of connectors 120 disposed on arm 110 can provide a minimal spacing distance between a first and second intravenous pole assembly connected with use of apparatus 100.

Figure 5:
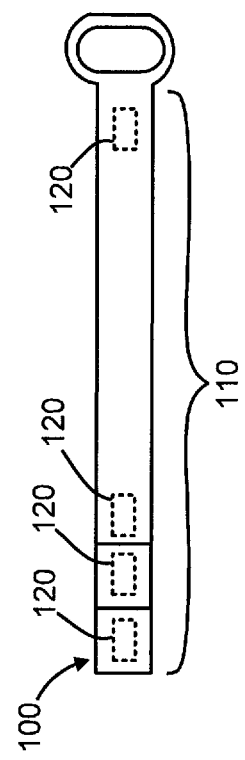
FIG. 5 is a front view of an apparatus in a compacted configuration for use in connecting a plurality of intravenous pole assemblies and comprising an arm in a compacted configuration having a plurality of telescoping members.

Referring to FIG. 5, FIG. 5 is a front view of apparatus 100 as shown in the prospective view of FIG. 3 except whereas in the embodiment of FIG. 3 apparatus 100 is shown in an expanded configuration, the telescoping member apparatus 100 is shown in a compacted configuration. A compacted configuration can be particularly useful to establish when apparatus 100 is used for connecting a limited number e.g., two intravenous pole assemblies or if apparatus 100 is in storage, e.g., in temporary storage at a central location (e.g., Central Service).

Figure 6:
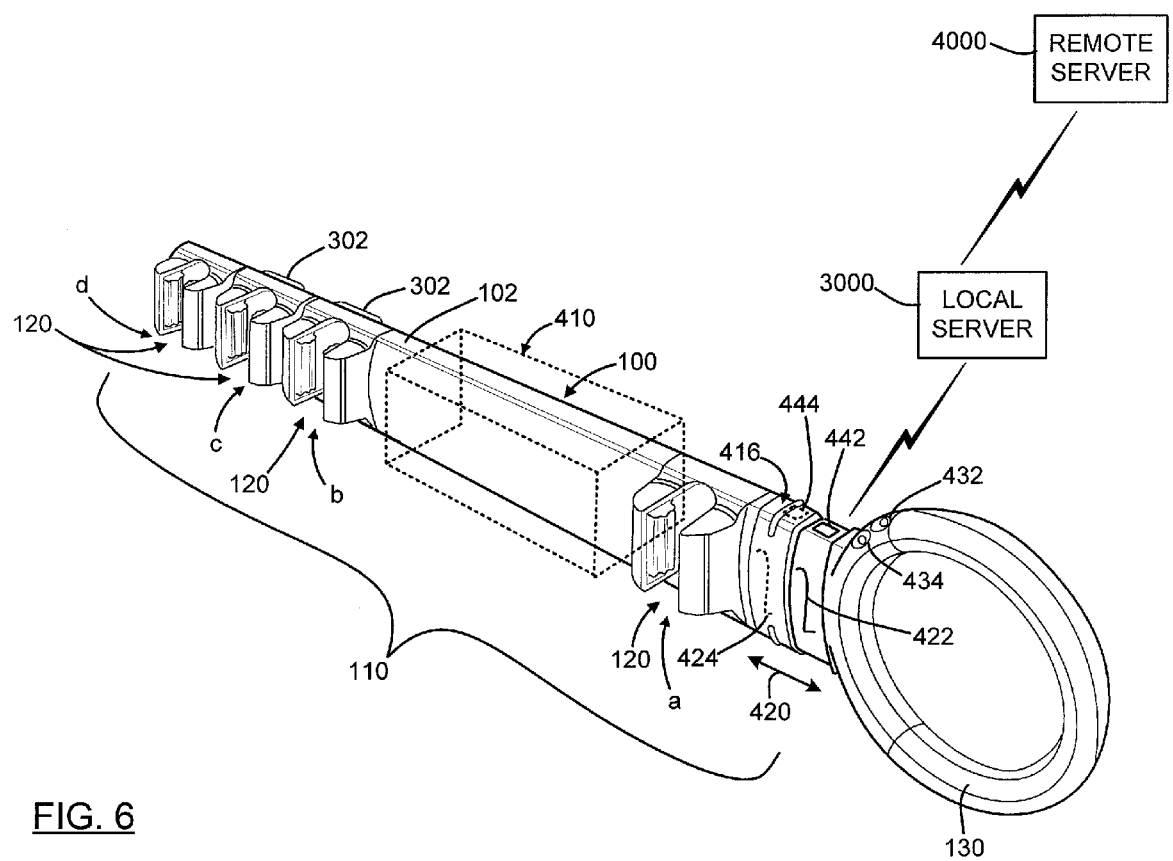
FIG. 6 is a perspective view of an apparatus for use in connecting a plurality of intravenous pole assemblies in which the apparatus includes an arm comprising a plurality of telescoping members and having disposed thereon a plurality of connectors disposed at spaced apart locations of the arm.

A perspective view of apparatus 100 in one particular embodiment is shown in FIG. 6. Apparatus 100 can include arm 110 and handle 130. Arm 110 can have disposed thereon a plurality of spaced apart connectors 120. In the embodiment of FIG. 6, apparatus 100 can include connector 120 at location "a;" a connector 120 at location "b;" a connector 120 at location "c;" and a connector 120 at location "d" as shown in FIG. 6. Apparatus 100 in the embodiment of FIG. 6 is a telescoping member apparatus of the type described with reference to FIGS. 3 and 5. In the view of FIG. 6 apparatus 100 is shown in a compacted configuration for use in connecting a limited number of intravenous pole assemblies or for storage.

Referring to two further features of apparatus 100 as shown in FIG. 6, apparatus 100 can include pressable buttons 302 as will be described further herein for establishing different lengths of arm 110 by way of adjustment of the extension length of telescoping members of apparatus 100. Connectors 120 in the embodiment of FIG. 6 are of a "roller clamp" style which can impart a spring loaded compression force to a pole of an intravenous pole assembly of which will be described later herein. In another aspect as will be set forth further herein, apparatus 100, in one embodiment, can be in communication with local external server 3000 and/or remote external server 4000.

Figure 8:
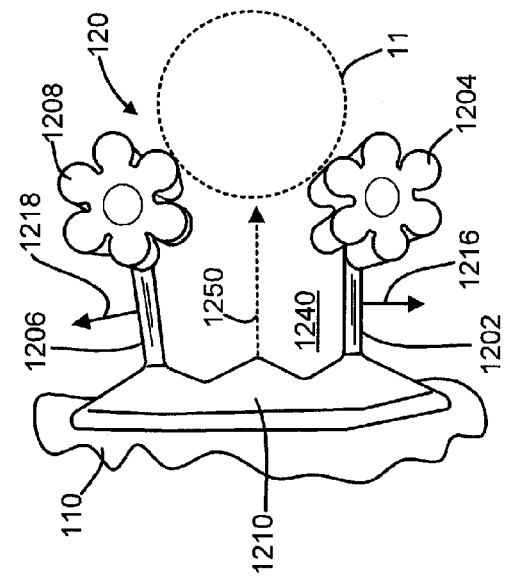
FIG. 8 is a top view of the connector as shown in FIG. 7.
Figure 7:
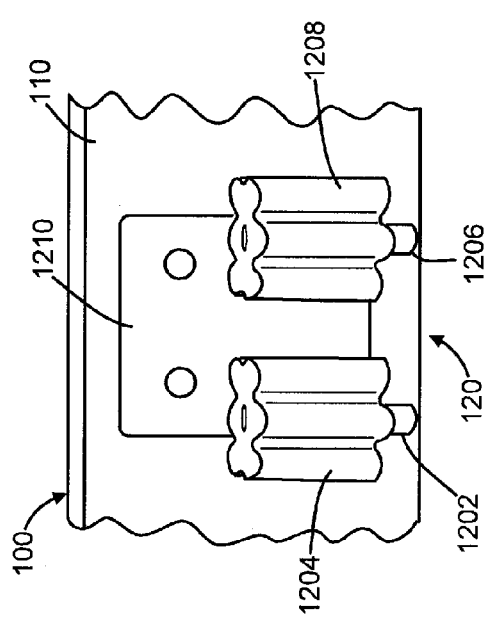
FIG. 7 is a front view of a connector for use in holding a pole of an intravenous pole assembly.

A "roller clamp" type connector for use with apparatus 100 and for connecting a pole of an intravenous pole assembly described with reference to FIGS. 7, 8, and 9. FIG. 7 shows a front view of a "roller clamp" type connector. FIG. 8 shows a top view of a "roller clamp" type connector, and FIG. 9 shows a top perspective view of a "roller clamp" type connector.

Figure 9:
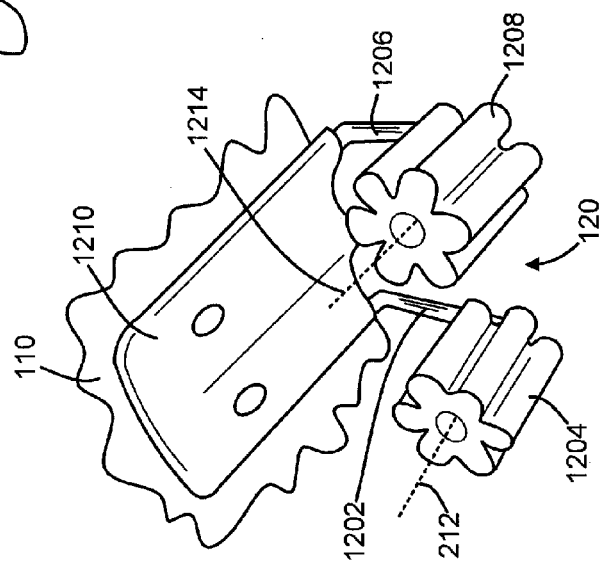
FIG. 9 is a perspective view of the connector as shown in FIG. 7.

Connector 120 as shown in FIGS. 7, 8, and 9 can include a pair of clamping members 1202, 1206. Clamping members 1202 and 1206 can extend from arm 110 and can support rollers 1204, 1208, rollers 1204, 1208 can be adapted to be rotational about axis 1212 and 1214 respectively. Clamping members 1202, 1206 can be of resilient construction so as to have an unstressed state as indicated in FIGS. 7, 8, and 9 but be capable of movement in the direction of arrows 1216 and 1218 (FIG. 8) to accommodate a connection of a pole assembly. Once a connection to a pole 11 is made, spring loaded clamping members 1202 can impart a spring loaded clamping (compression) force to pole 11 for retaining of pole 11, which force can be transferred to rollers 1204, 1208. Connector 120 can be configured so that rollers 1204, 1208 but not members 1202, 1206 contact pole 11 when a connection is complete for retaining of pole 11. Connector 120 can also be configured so that both rollers 1204, 1208 and members 1202, 1206 contact pole 11 for retaining of a pole 11 when a connection is complete. It should be noted that in one embodiment of the connector 120 as shown in FIGS. 7-9, connector 120 need not impart substantial or any compression force to pole 11 when a connection is complete. Specifically, where a pole diameter is sufficiently small, connector 120 as shown in FIGS. 7-9 can provide a connection for retain of a pole 11 without imparting a compression force to pole 11 simply by retaining a pole 11 so that pole 11 is restricted from moving out of pocket 1240. For achieving such functionality, connector 120 can be configured so that a gap between rollers 1204, 1208 when connector 120 is in an unstressed state is of a distance that is greater than a diameter of pole 11 to which connector 120 is connected.

An exemplary method for connecting connector 120 to a pole assembly is described with reference to FIG. 8. Connector 120 can be connected to pole 11 of a certain intravenous pole assembly by first contacting rollers 1204 and 1208 to a surface of pole 11, e.g. by manually moving one or more of apparatus 100 and the certain intravenous pole assembly. Connector 120 can then be manually moved relative to pole 11 in the direction of the arrow of connection axis 1250 for achieving a connection. When connector 120 is manually moved relative to pole 11 in the direction of the arrow of connection axis 1250 clamping members 1202 and 1206 spread outwardly slightly in the direction of arrows 1216, 1218 to allow accommodation of pole 11 into pocket 1240 defined by members 1202, 1206 as well as rollers 1204 and 1208. While connector 120 is moved along connection axis 1250 in the direction of the arrow of axis 1250, rollers 1204 and 1208 can rotate slightly to allow entry of pole 11 into pocket 1240. Pole 11 is received into pocket 1240 and clamping members 1202 and 1206 are urged into their unstressed state and therefore impart a compression force onto pole 11 for retaining of pole 11.

Referring to connector 120 of FIG. 8 symmetrically arranged as shown in FIG. 8, a connection axis 1250 of connector 120 can be regarded as the axis defining a relative direction which the connector 120 can be moved relative to pole 11 to achieve a connection between connector 120 and pole 11. It will be seen that if apparatus 100 is maintained stationary and a manually generated force is imparted so that pole 11 is moved in a direction opposite the arrow of axis 1250, the relative direction between apparatus 100 and pole 11 will be the direction along axis 1250 of FIG. 8 opposite the direction indicated by the arrow shown on axis 1250 (FIG. 8).

Figure 10:
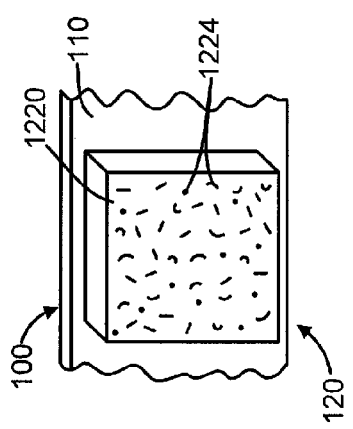
FIG. 10 is a front perspective view of a connector for use in holding a pole of an intravenous pole assembly of another configuration.

Referring now to FIG. 10, another embodiment of connector 120 is shown and described. In the embodiment of FIG. 10, connector 120 can be provided by a pad 1220 which engages a pole 11 to retain a pole 11 of an intravenous pole assembly by way of magnet forces. A pole 11 of an intravenous pole assembly typically comprises steel and accordingly can be retained with use of magnet forces.

Still referring to the embodiment of FIG. 10, pad 1220 in addition to including magnetic material capable of magnetically attracting a steel intravenous pole can include adhesive 1224 for adhesively engaging and thereby retaining a pole of intravenous pole assembly.

In another embodiment, pad 1220 can include adhesive 1224 but may not comprise magnetic material (may be devoid of magnetic material).

In another embodiment, pad 1220 can comprise magnetic material but may not comprise adhesive 1224 (may be devoid of adhesive material).

It will be understood that one or both of magnetic material and or adhesives can be incorporated to the remaining embodiments of connectors 120 described herein for increasing the retaining forces for retaining a pole 11 provided by the connector 120. A pad type connector 120 as described with reference to FIG. 10 can be connected to a certain intravenous pole assembly by manually imparting a force to one or more of an apparatus 100 and a certain intravenous pole assembly so that the connector 120 connects to a pole 11 of the certain intravenous pole assembly for retaining of the pole 11.

Figure 11:
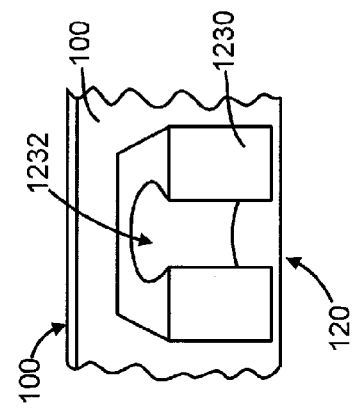
FIG. 11 is a front perspective view of a connector for holding a pole of an intravenous pole assembly according to an alternative configuration.
Figure 15:
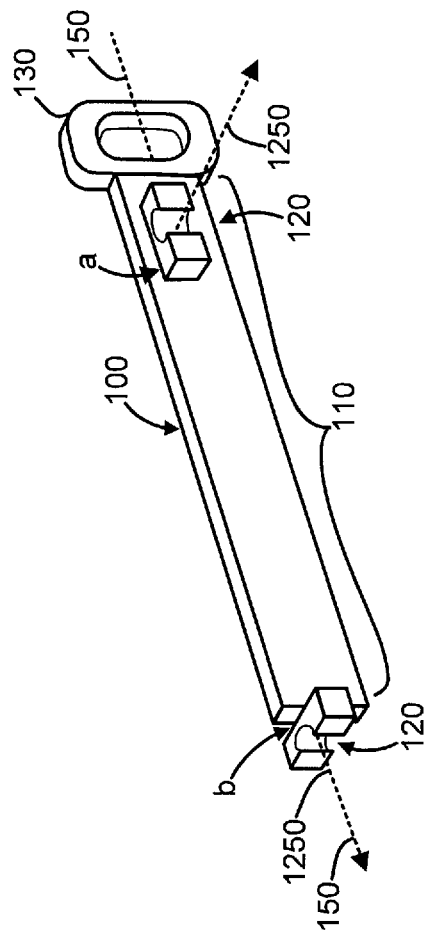
FIG. 15 is a perspective view of an apparatus for use in connecting a plurality of intravenous pole assemblies having a connector that includes connection directions which extends generally in a direction of an axis of an arm included on an apparatus.

Referring now to the connector 120 as shown in FIG. 11, connector 120 can operate to connect and retain a pole 11 by way of imparting forces on pole 11 including spring loaded compression forces and in one embodiment, operate similarly to the connector 120 of FIGS. 7-9. Connector 120 of FIG. 11 can include a resilient pad 1230 which defines a pocket 1232. With pad 1230 being made of resilient material, the edges of pad 1230 defining the opening of pocket 1232 can deform to allow entry of pole 11 to a position within pocket 1232. Pocket 1232 in an unstressed state can be sized to have a diameter slightly smaller than an expected diameter of pole to which it can connect, so that there can be achieved an interference fit between a pole 11 and the connector 120 for providing a retaining of a pole 11. With such interference fitting, connector 120 can impart a spring loaded compression force to pole 11 for retaining of a pole 11. In one embodiment pocket 1232 can be sized to have a smaller diameter than an expected diameter of a pole 11 to which it can connect. Once engaged within pocket 1232 the surfaces of pad 1230 defining the pocket 1232 can move toward their unstressed state to impart a spring loaded compression force to pole 11 within pocket 1232 for retaining of a pole 11. It should be noted that in one embodiment of the connector 120 as shown in FIG. 11, connector 120 need not impart substantial or any compression force to pole 11 when a connection is complete. Specifically, where a pole diameter is sufficiently small relative to a diameter of pocket 1232 in an unstressed state, connector 120 as shown in FIG. 11 can provide a connection for retaining of a pole 11 without imparting a compression force to a pole 11 simply by retaining a pole 11 so that pole 11 is restricted from moving out of pocket 1232. For achieving such functionality, connector 120 can be configured so that pocket 1232 in an unstressed state has a diameter of greater than a diameter of a pole 11 to which connector 120 is connected. Connector 120 as shown in FIG. 11 can be adapted so that connector 120 can be connected to a certain intravenous pole assembly by manually imparting a force to one or more of apparatus 100 and the certain intravenous pole assembly so that connector 120 and a pole 11 of the certain intravenous pole assembly are moved relative to one another in a direction of connection axis 1250 as shown in FIG. 15 until a connection is made between connector 120 and pole 11.

Poles 11 of intravenous pole assemblies commonly have diameters ranging from about 0.75 inches to about 1.00 inches (1.91 cm to about 2.54 cm). In one embodiment, a connector 120 of a type set forth herein having a spring loaded pocket, e.g., of the embodiment of FIGS. 7-9, or of the embodiment of FIG. 11 can have an unstressed state diameter of less than a diameter of the smaller end range of pole diameter expected to be encountered in an operating environment (less than 1.91 cm in the described embodiment). In such manner, connector 120 can impart a compression force to smaller dimensioned poles encountered in an operating environment.

Figure 13:
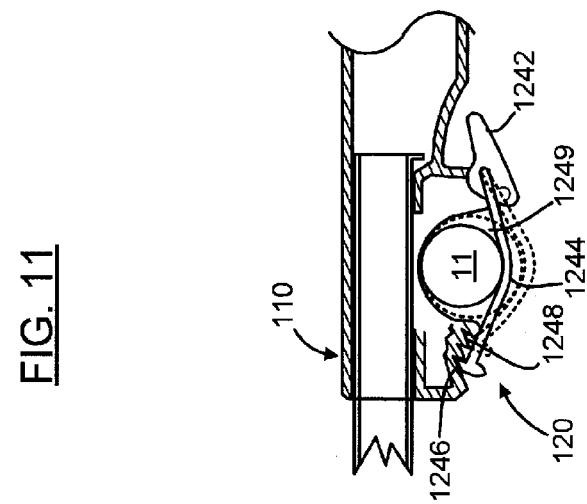
FIGS. 12 and 13 are top schematic views of a connector for holding a pole of an intravenous pole assembly according to an alternative configuration.
Figure 12:
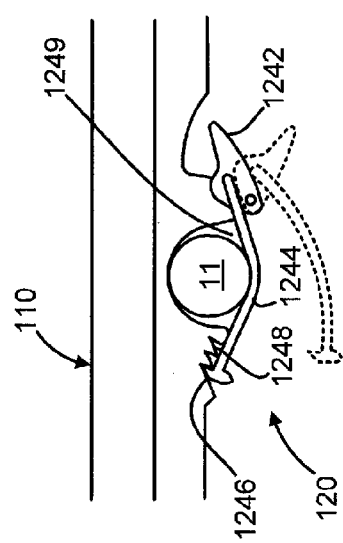

Referring now to the embodiment of FIGS. 12 and 13, a lever clasp (ski boot) type connector 120 is described. The connector in the embodiment of FIGS. 12 and 13 includes a pivotally mounted lever 1242 which is operationally connected to clasp 1244. Clasp 1244 can include claw 1246 which can engage in saw tooth formation 1248 of arm 110. For connection and retaining of a pole 11 within pocket 1249, pole 11 can be deposited within pocket 1249 via manual movement of apparatus 100 and/or an intravenous pole assembly and then clasp 1244 can be manually moved to engage onto saw tooth such that claw 1246 is engaged into saw tooth formation 1248. Lever 1242 can then be manually pressed in to engage pole 11 within pocket 1249. When in a closed position the connector 120 as shown in FIGS. 12 and 13 can extend 360 degrees about a pole 11 to which it can be connected for retaining of pole 11 within pocket 1249. In one embodiment, surfaces defining pocket 1249 impart a compression force to pole 11 for retaining pole 11. In another embodiment, surfaces defining pocket 1249 can retain pole 11 without imparting compression force thereto by restricting movement of pole 11 out of pocket 1249.

Use of connectors 120 as shown in the embodiment of FIGS. 12 and 13 can be particularly useful where a group of intravenous pole assemblies is to be transported over a rough surface e.g., a shag carpet, a paved or dirt road, e.g., as in a temporary health care facility. In numerous applications however a pole 11 can be held within a connector 120 with minimal holding forces and for connecting a group of intravenous pole assemblies and a connected group so connected can be successfully transported as a group. A risk of an intravenous pole assembly becoming disconnected can be expected to be reduced where a group is to be transported over a smooth flat surface.

In one embodiment, a connector 120 as set forth herein can be configured to impart forces on a pole 11 having characteristics so that (a) a connected apparatus 100 remains at a certain elevation (e.g., the elevation of apparatus 100 at the time of connection of a pole 11) during transport of a connected group of intravenous pole assemblies and (b) a connected pole 11 retained by the connector is allowed to rotate about an axis of a pole while in a state of being connected and retained. Such connection provides for a desired physical association between assemblies while allowing flexibility of movement of a group of intravenous pole assemblies, thus enhancing the ease with which a group of connected intravenous pole assemblies can be moved across a horizontal surface in a variety of directions without disruption of a connection of the group. If some rotation of a pole within a connector is allowed without a connection being broken, a risk of a connection being broken can be reduced in some embodiments. A roller clamp configuration for connector 120 as shown in FIGS. 7-9 can be particularly advantageous for allowing rotational movement of a pole 11 while remaining connected by connector 120 for the reason that rollers 1204, 1208 can reduce fiction forces between a connector 120 and a pole 11 which might otherwise resist a rotation of a pole. A similar result can be achieved in an embodiment such as in FIG. 11 by configuring surfaces defining pocket 1232 to be smooth for reduced friction. In some embodiments, strong friction force between connector 120 and a pole 11 may be desired.

It will be seen that, notwithstanding that it may be advantageous to provide connector 120 to allow rotation of a pole therein, a group of connected intravenous pole assemblies can be configured to allow rotation of a certain pole 11 about its axis without an orientation of a connector 120 to the certain pole changing. Specifically, by the operation of wheels 13, a pole 11 can rotate about its axis with an orientation of connector 120 connected to the pole 11 remaining constant. By virtue of the freedom of motion provided by wheels 13, forces imparted to a group of connected intravenous pole assemblies which might otherwise break a connection between a connector 120 and a pole 11 can be transferred to cause movement of rotatably mounted wheels without a loss of connection between a connector 120 and a pole 11.

In one embodiment, one or more intravenous pole assembly can be adapted for facilitating or augmenting a connecting between a connector and one or more intravenous pole assemblies. In one example, a section of microloop and hook fastener material can be wrapped about each of a pair of first and second poles of intravenous pole assemblies to be connected. Apparatus 100, in such embodiment, can have disposed therein first and second connectors provided by sections of microloop and hook fasteners that are adapted to mate with the sections of microloop and hook fasteners disposed on the first and second intravenous pole assemblies. A group of connected intravenous pole assemblies can be defined by connecting the first connector to the section of the first intravenous pole assembly and the second connector to the section of the second intravenous pole assembly. In one embodiment, an entire length of arm 110 can have disposed thereon an elongated unitary section of microloop and hook fastener material to define a plurality of connectors disposed on arm 110. Accordingly, in some embodiments a method can comprise disposing an adaptation on an intravenous pole assembly, the adaptation for use in connecting with a connector of an apparatus. However, in other embodiments as set forth herein, a method can be devoid of disposing on an intravenous pole assembly an adaptation for use in connecting with a connector of an apparatus, thus facilitating use of a method with intravenous pole assemblies having no specialized adaptations.

A connector 120 as set forth herein can be adapted so that connector 120 is releasably connectable (detachable attachable) with respect to an intravenous pole assembly with use of a manually generated force. Where connector 120 is of a type having a connection axis 1250, connector 120 can be adapted so that connector 120 can be connected to a pole 11 of a certain intravenous pole assembly by manually imparting a force to one or more of apparatus 100 and the certain intravenous pole assembly to move connector 120 and pole 11 toward one another in a direction along connection axis 1250 until connector 120 and pole 11 are connected together. Where connector 120 is of a type having a connection axis 1250 as set forth herein, connector 120 can be adapted so that connector 120 can be released from an intravenous pole assembly by manually imparting a force (e.g., imparted at one or more of apparatus 100 and the certain connected intravenous pole assembly) to move connector 120 away from pole 11 in a direction along connection axis 1250.

"Pad type" connectors 120 such as those described with reference to FIG. 10 can be adapted so that connector 120 can be released from a pole 11 of an intravenous pole assembly by imparting a manually imparted force, e.g. to apparatus 100 and/or a connected intravenous pole assembly, to move connector 120 in a direction away from a connected pole 11. A lever clasp type connector 120 as shown in FIGS. 12 and 13 can be manually released by manually opening clasp 1244 and then manually imparting a force to move connector 120 away from pole 11.

It has been described that connector 120 can be adapted to be releasably connected with a pole 11 of an intravenous pole assembly with use of manually generated forces. In another aspect, e.g., where connector 120 is of a style having a connection axis 1250, or where connector 120 is of a "pad" style as shown in FIG. 10 or where connector 120 comprises a section of microloop and fastener material, it is seen that connector 120 can be adapted so that connector 120 can be manually connected to a pole 11 of a certain intravenous pole assembly with use of a single direction manually imparted push force manually imparted at apparatus 100 and it is further seen that connector 120 can be adapted so that connector 120 can be manually released from pole 11 of a certain intravenous pole assembly with use of a single direction pull force manually imparted at apparatus 100.

Figure 14:
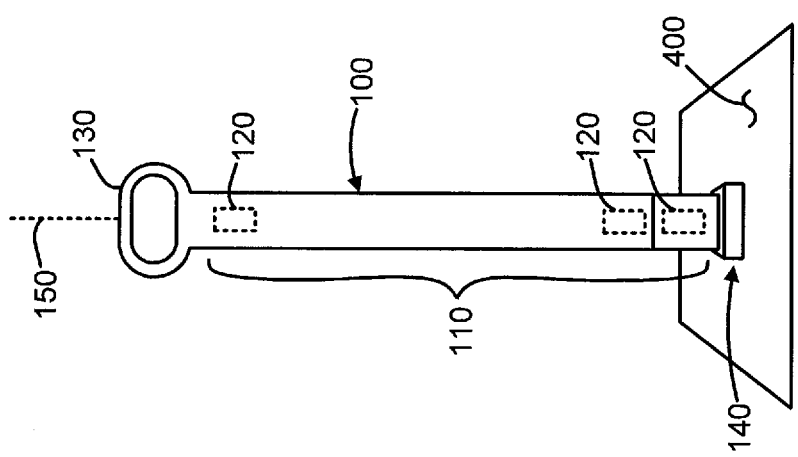
FIG. 14 is a schematic view of an apparatus for use in connecting a plurality of intravenous pole assemblies wherein the apparatus is adapted to be standed (stood) vertically on a horizontal surface.

Referring now to the embodiment of FIG. 14, the embodiment of FIG. 14 apparatus 100 can be configured, e.g., appropriately balanced and shaped so that apparatus 100 can be standed on a horizontal surface 400 (without support of an external member), e.g., a floor by contacting of distal end 140 of apparatus 100 on the horizontal surface 400 and positioning arm 110 vertically. In the embodiment of FIG. 14 apparatus 100 can be adapted to be standed vertically on a horizontal surface, e.g., a floor at a health care worker's work station Without outside securing mechanisms in such manner that arm 110 extends upwardly vertically to define a "ready" position; a position in which apparatus 100 is easily grasped by an operator for use in connecting to an intravenous pole assembly. For such operation in one embodiment a distal end 140 can include one or more planar surfaces that extend in a direction generally transverse to an axis 150 of arm 110. As shown in FIG. 14, when apparatus 100 is in a ready position, a highest point of apparatus 100 can be defined by handle 130. With such position, handle 130 can be at a position that is closest to an eye and a hand of an operator. In one embodiment, a ready position can be defined by configuring apparatus 100 to be free standable on a horizontal surface without external support with arm 110 extending upwardly relative to a horizontal surface 400 supporting apparatus 100. Such configuration can be achieved, e.g., by weighting distal end 140 to be substantially heavier than a remainder of apparatus 100 and by appropriately shaping of distal end 140, e.g., to include a planar distal end surface. There is set forth herein an apparatus shaped and balanced as to be capable of being free standed on a horizontal surface in such manner that arm 110 extends upwardly.

In the embodiment of FIG. 15, apparatus 100 can include an arm 110 and a handle 130. Arm 110 includes a first connector 120 disposed at location "a" and a second connector 120 disposed at location "b." However in the specific embodiment of FIG. 15, connector 120 at location "a" has a connection axis 1250 as explained herein that extends in a direction substantially perpendicular to an axis 150 of arm 110 while connector 120 at location "b" has a connection axis 1250 that extends substantially in a direction of axis 150 of arm 110. Connectors 120 as shown in the embodiment of FIG. 15 are provided by the type of connectors described with reference to FIG. 11 but could also easily be provided by a connector 120 as described in the embodiment of FIG. 10 or by a connector 120 as described in the embodiment of FIGS. 7-9. It is seen that connector 120 at location "b" of apparatus 100 has a connection axis 1250 extending generally in the direction of axis 150. In the specific embodiment shown, connector 120 at location "b" has connection direction substantially in common with a direction of axis 150, and a path coextensive with axis 150. If connector 120 is offset from axis 150, connector 120 at location "b" can have a connection direction substantially in common with axis 150 and a path parallel to axis 150.

By the configuration as shown in FIG. 15, apparatus 100 of FIG. 15 is adapted for simplified single handed connection to an intravenous pole assembly. With reference to the configuration as shown in FIG. 15, arm 110 and connector 120 at location "b" can be complementarily configured so that the connector 120 at location "b" can be connected to a pole of an intravenous pole assembly by moving apparatus 100 in a compass direction in common with a compass direction of axis 150 of arm 110 (axis 150 having first and second opposite compass direction). That is, for connection of apparatus 100 as shown in FIG. 15 to an intravenous pole assembly having a pole 11, apparatus 100 can be moved by an operator in a direction by using a single handed "poking" motion. Such simplified single handed connecting operation would not be affected by an offsetting of connector 120 from axis 150 while maintaining a connection axis 1250 of connector 120 at location "b" substantially parallel with axis 150. (In fact, it is seen that with such offsetting, the compass directions of the apparatus motion and of axis 150 remain in common). In the case involving the embodiment of the apparatus in FIG. 15, connector 120 at location "b" can first be connected to a first intravenous pole assembly by use of the aforementioned "poking" motion and then a second intravenous pole assembly can be moved into proximity of a second connector 120 at location "a" for engagement of connector 120 at location "a" to the pole 11 of the second intravenous pole assembly. It is seen with reference to the embodiment of FIG. 15 that connector 120 at location "b" can be appropriately shaped, e.g., with planar end surfaces appropriately weighted and/or disposed transverse to axis 150 and a remainder of apparatus 100 configured so that apparatus 100 has the characteristics as shown in FIG. 14 such that apparatus 100 can be free standed on a horizontal surface such that arm 110 extends upwardly, with a highest portion of apparatus 100 being defined by handle 130.

Figure 16:
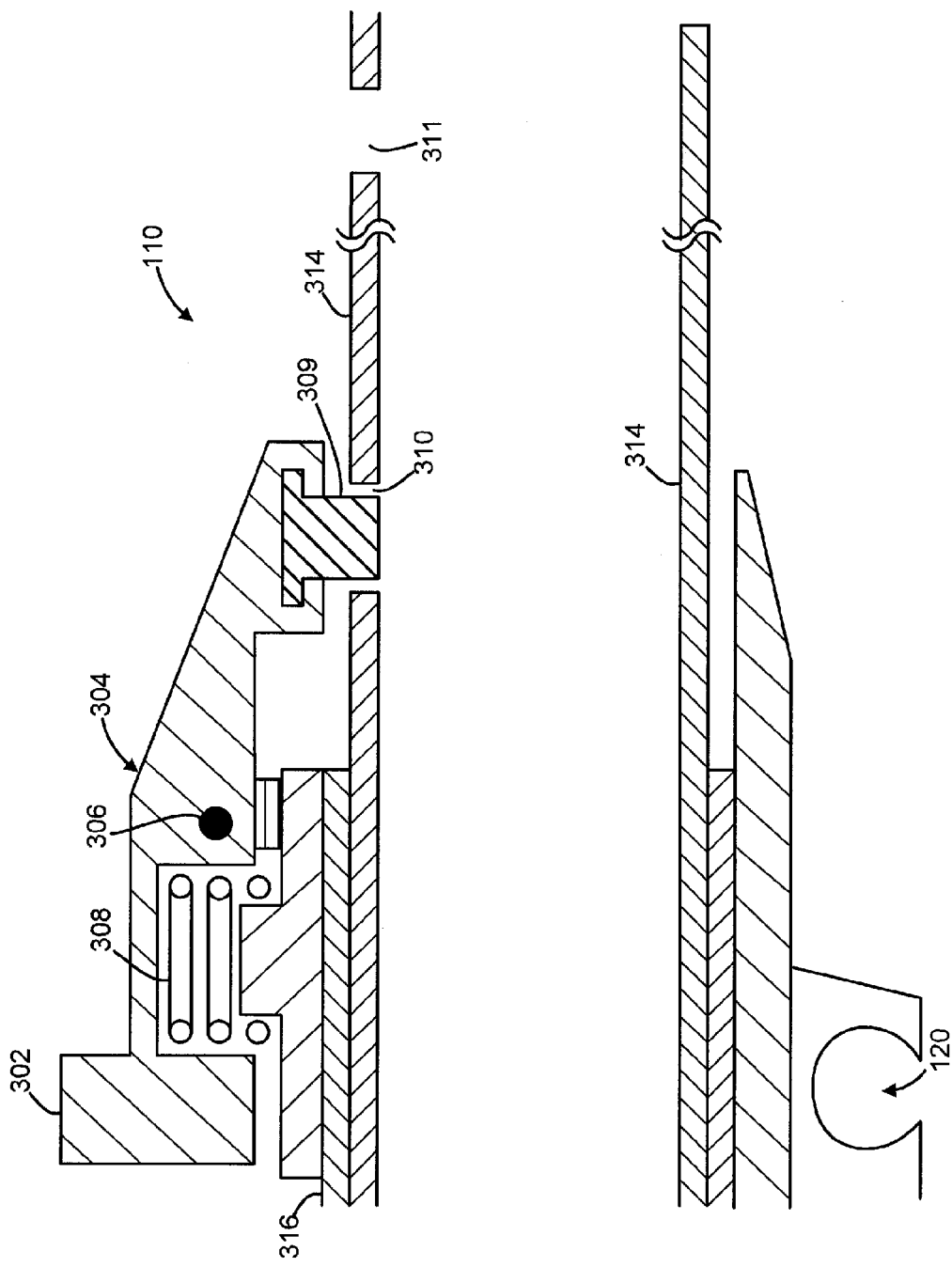
FIG. 16 is a cross-sectional top view of an arm of an apparatus for use in connecting a plurality of intravenous pole assemblies wherein the arm includes a spring loaded mechanism for extending the length of an arm having an arm which comprises a plurality of telescoping members.

Referring to FIG. 16, a spring loaded mechanism for achieving adjustment of a length of a telescoping arm is described. The telescoping arm 110 as described in FIG. 16 can include a pressable button 302 which forms part of a lever 304 that is associated to pin 309. Lever 304 can be pivotally arranged on arm 110 with use of pivot point 306. The described mechanism can also include spring 308 normally biasing a lever 304 into a position in which pin 309 pivoted downward to engage into detent 311. Telescoping member 314 of arm 110 can have a plurality detents e.g., detent 310 and detent 311. Detent 310 in which pin 309 is positioned determines the current length of the extended arm 110. For adjustment of the length of telescoping arm 110 the pressable button 302 can be pressed downward. Such action results in lever 304 pivoting about pivot point 306 to disengage pin 309 from detent 310. A position of telescoping member 314 within surrounding member 316 can then be adjusted e.g., telescoping member 314 can be pushed inwardly so that pin 309 is located above second detent 311. When a new desired relative position of member 316 and member 314 is achieved, the pressable button 302 can be released again so that pin 309 engages detent 311 associated with the second desired position.

In the use case described with reference to FIG. 17, a plurality of apparatuses 100 are used in a large number of intravenous pole assemblies, specifically six assemblies 10, 20, 30, 40, 50, 60 in the specific embodiment shown.

In the use case described, three apparatuses 100, each of a different style are used to connect the six assemblies. However in another embodiment it is understood that each apparatus 100 could be of a common style.

Referring to apparatus 100 at location I, apparatus 100 at location I is shown in a position in which it connects assemblies 10, 20, and 30. Further, it is seen that connector 120 at a distal end of apparatus 100 is of the type described having a connection axis including a compass direction coinciding with axis 150 of apparatus 100 allowing simplified single handed operation for connection.

Referring to apparatus 100 at location II, apparatus 100 is shown as being of a style that is not reconfigurable between composed and expanded configurations and which includes two connectors 120 is described herein with reference to FIG. 1. Apparatus 100 at location III of FIG. 17 is shown as including an arm 110 with a single telescoping member for achieving an adjustment in a length of arm 110. It will be seen with reference to the use case illustrated in FIG. 17 that an unlimited number of apparatuses of intravenous pole assemblies can be connected together by adding additional apparatuses 100 and assemblies. It may be desirable to transport large groups of intravenous pole assemblies in a variety of applications including e.g., applications in which intravenous pole assemblies are moved about within a central location. It is seen with reference to the use case illustrated in FIG. 17 that a connector 120 of an apparatus 100 can be connected to an intravenous pole 11 at a position of a pole 11 above a base 12 from which the pole extends.

In one embodiment a connector can be connected to a pole 11 at a height of a pole 11 that is more than ten percent of the total pole height. In one embodiment, a connector 120 can be connected to a pole 11 at a height of a pole 11 that is more than twenty percent of the total pole height. In one embodiment, connector 120 can be connected to a pole 11 at a height of pole 11 that is more than thirty percent of the total pole height. In another embodiment connector 120 can be connected to a pole 11 at a height of pole 11 that is more than forty percent of the total pole height. In one embodiment, connector 120 can be connected to a pole 11 at a height of pole 11 that is more than fifty percent of the total pole height.

Figure 17:
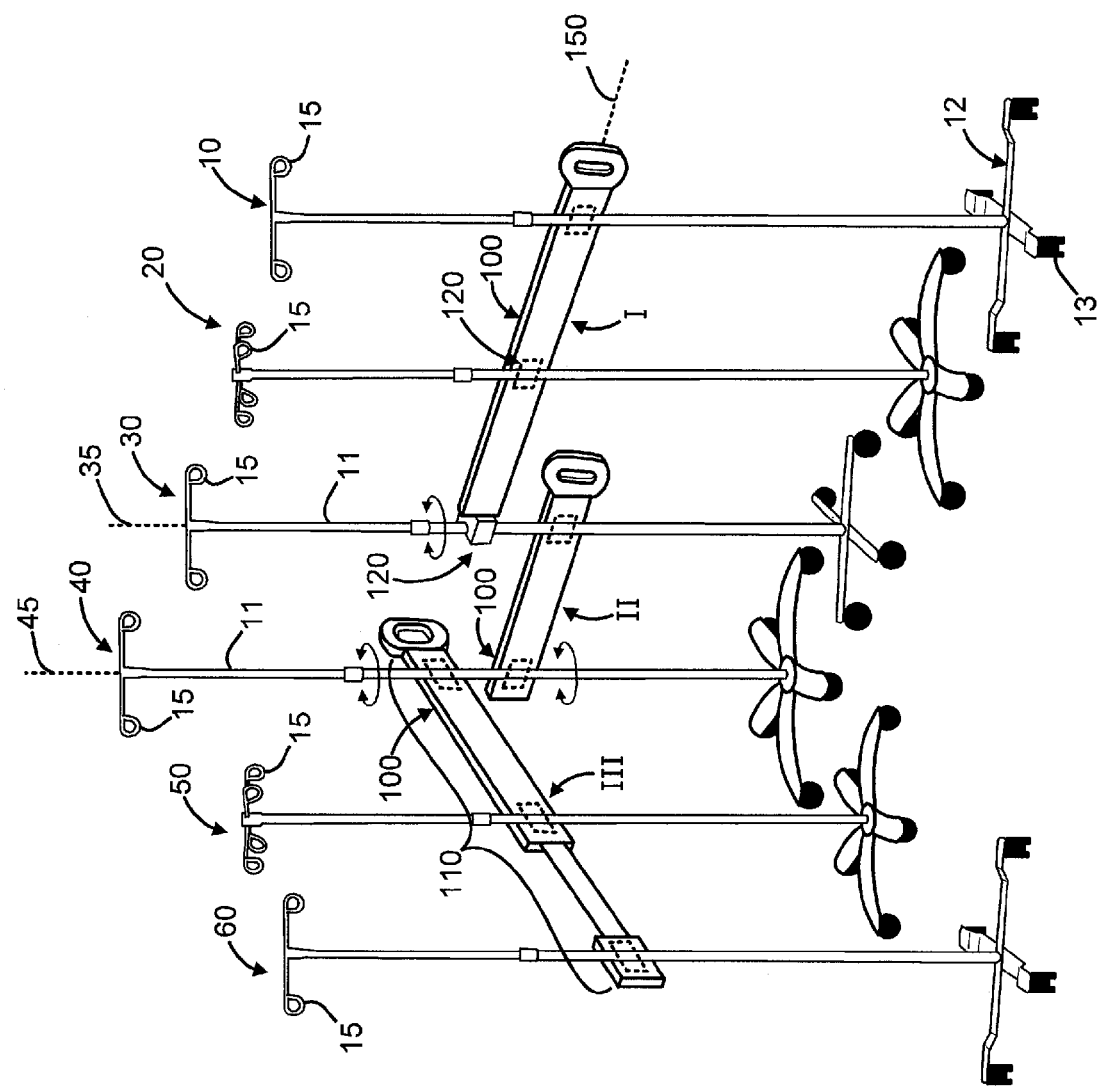
FIG. 17 is a perspective use case view illustrating a plurality of apparatuses for use in connecting a plurality of intravenous pole assemblies and a plurality of apparatuses are deployed for defining a group of connected intravenous pole assemblies wherein the group comprises first, second, third, forth, fifth, and sixth intravenous pole assemblies.

With reference to the use case depicted in FIG. 17, it will be seen that the plurality of connected intravenous pole assemblies can be capable of pivoting about an axis 35 defined by the pole 11 of intravenous pole assembly 30 and also about axis 45 defined by the pole 11 of intravenous pole assembly 40. Accordingly, the group of intravenous pole assemblies depicted by FIG. 17 is capable of achieving a variety of different configurations, i.e., orientations between the various intravenous pole assemblies. Such functionality can be highly useful e.g. in the instance the group of connected intravenous pole assemblies is to be moved through a narrow width door, onto and out of a narrow width elevator, around a narrow hallway, around fixed medical equipment or furniture and the like.

Examples of groups of connected intravenous pole assemblies are shown in FIGS. 1, 2, 3, and 17. For movement of a group of connected intravenous pole assemblies, a variety of methods can be employed. For example, a pulling force can be imparted at a handle 130 of one apparatus 100, e.g., by manually grasping of handle 130 and pulling. A pushing force can be imparted at a handle 130 of apparatus 100, e.g., by manually grasping of handle 130 by an operator and pushing. Also pulling or pushing forces to move a group of connected intravenous pole assemblies can be imparted at one apparatus 100 at a location other than handle 130, e.g., by an operator grasping apparatus 100 at a location other than handle 130 and then pulling or pushing. Further, a group of connected intravenous pole members can be moved by imparting forces at location of a connected group other than an apparatus 100. For example, a pulling or pushing force can be manually imparted at one or more intravenous pole assembly poles 11 of a connected group of intravenous pole members, or at one or more bases 12 of a connected group of intravenous pole assemblies. Such imparting of forces can comprise grasping of one or more intravenous pole assemblies by an operator who may then impart the pulling or pushing force. With use of the described method, a connected group of intravenous pole assemblies can have substantial freedom of movement. In one embodiment, one or more apparatus 100 can be rotatably about one or more pole 11. Also, by their common configuration with rotatable wheels 13 can be capable of motion in any direction and can be capable of rotation.

In another aspect, apparatus 100 can be color coded to designate an intended area of use of an apparatus 100. In one embodiment, with reference to the specific embodiment of FIG. 6, surfaces of apparatus 100 within area 410 and/or additional surfaces can be colored a specific color to designate a specific intended area of use of apparatus 100. Some areas of a hospital, e.g., an infectious disease area or Methicillin-resistant Staphylococcus aureas (MRSA) areas are at relatively higher risk of attracting infection. Accordingly in the development of apparatus 100 it was determined, that there is a special advantage to having the capacity to readily determine by simple visible observation that apparatus 100 is properly commissioned in such higher risk areas, namely to reduce a likelihood of an unintended movement of apparatus 100 into other areas. In other high susceptibility areas of a hospital, e.g., pediatrics, patients are at a special risk of suffering negative consequences as a result of exposure to infection. In the development of apparatus 100, it was determined that there is a special advantage to having the capacity to readily determine by visual observation that apparatus 100 has not been improperly commissioned in such high susceptibility areas, namely, to reduce the spread of infectious disease. A possible color scheme for color coding of apparatus 100 according to intended use schemes is provided below.

TABLE 1

| Area | Color |
|---|---|
| Infectious Disease | Purple |
| Pediatrics | White |
| Surgery | Blue |
| Neonatal Intensive Care | Yellow |
| Emergency | Red |

In another aspect, apparatus 100 can be configured to include a user adjustable status indicator for indicating a status condition of apparatus 100. In one example, a status indicated by apparatus 100 can be responsive to manual action by a user. A status condition indicated by apparatus 100 can be a clean/dirty status (i.e., disinfected/not disinfected) or an operation status, e.g., operational, or broken. In one management method, such status can be regarded as a status of apparatus 100. In another management method, a status indicated by apparatus 100 can be regarded as a status of a group of one or more intravenous pole assemblies connected with use of apparatus 100.

Status indicating features of apparatus 100 in one embodiment are described with reference to FIG. 6. In one embodiment, apparatus 100 can include a moveable opaque collar 416 moveable in compass directions given by arrows 420. When collar 416 is in the position shown in FIG. 6, surface 422 is visible to a user. When collar 416 is moved to a position to cover surface 422, surface 424 indicated as dashed lines in FIG. 6 is visible. In one embodiment, surface 422 and surface 424 can bear different visible colors. In one example, surface 422 can be green and surface 424 can be red. In one management method, green can be regarded as the color indicating clean/disinfected and red can be regarded as a color indicating dirty/not disinfected state. Accordingly, by way of a user manually moving collar 416 leftward on apparatus 100, a user is able to change a status indicated by apparatus 100 from dirty/infected to clean/disinfected. By way of a user manually moving collar 416 rightward on apparatus 100, a user is able to manually change a status indicated by apparatus 100 from clean/disinfected to dirty/infected. In one management method, a user can make such change at a time when apparatus 100 is dispatched to a central location from a patient use location or from a central location to a patient use location so that when a connected group of intravenous pole assemblies is being transported, its status is known and easily visibly observable.

It has been described that a status indicated by apparatus 100 can be manually controlled by way of a user manually adjusting a mechanical feature of an apparatus. In another aspect, a status indicated by apparatus 100 can be electronically recorded and/or electronically indicated with use of one or more light source and/or a display.

In one embodiment as shown in FIG. 6, apparatus 100 can include status light sources (e.g., LEDs) 432 and 434. Light source 432 can be a green LED and light source 434 can be a red LED. The light sources 432, 434 can be controlled to indicate a status of apparatus 100. Light sources 432, 434 can supplement a status indicated by surfaces 422, 424 or can replace a status indication indicated by surfaces 422, 424.

Apparatus 100 can be configured so that when collar 416 is in the position as shown in FIG. 6, green light source 432 is energized and red light source 434 is de-energized. Apparatus 100 can be further configured so that when collar 416 is in the position to cover surface 422, red light source 434 is energized and green light source 432 is de-energized to indicate the status of apparatus (e.g., dirty/infected). For providing such functionality, apparatus 100 can be provided to include photodetectors 442, 444. When photodetector 442 is exposed to light, apparatus 100, by processing signals generated by photodetector 442, can determine that collar 416 is in the position shown and can energize green light source 432. When photodetector 444 is exposed to light, apparatus 100 can determine by processing signals generated by photodetector 444 that collar 416 is in a position covering surface 422 and can accordingly energize red light source 434.

Figure 18:
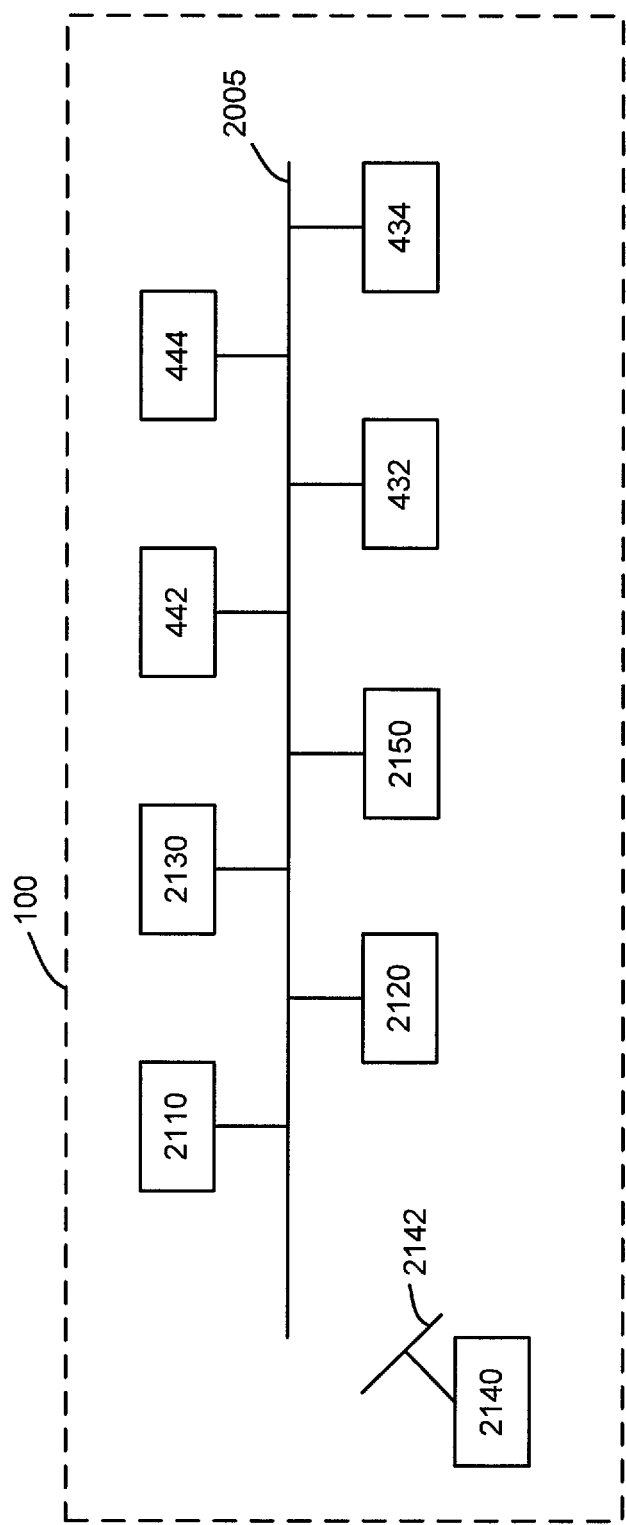
FIG. 18 is a block electrical diagram of an apparatus for use in connecting a plurality of intravenous pole assemblies, in one embodiment, wherein the apparatus is configured for communication with one or more external servers.

An electrical circuit block diagram of apparatus 100 in one embodiment is shown in FIG. 18. Apparatus 100 can include a central processing unit (CPU) 2110 and memory 2120 coupled together via system bus 2005. Light sources 432 and 434 as well as photodetectors 442 and 444 can be coupled to system bus 2005 for communication with CPU 2110. CPU 2110 can be configured using an appropriate software program to process signals generated by photodetectors 442 and 444 to determine a position of collar 416. CPU 2110 can be operative so that responsively to a determination of a position of collar 416, CPU 2110 controls energizing of a select one of light source 432 or light source 434. Referring to further aspects of apparatus 100, apparatus 100 can include a battery 2140 coupled to a power grid 2142 for powering electrical components of apparatus 100. CPU 2110 can be incorporated as part of a microcontroller or a microprocessor. Apparatus 100 can also include electronic display 2130. The components of FIG. 18 can be supported within housing 102 (FIG. 6) of apparatus 100.

In another aspect, a status of apparatus 100 (e.g., dirty/clean, operational/broken) can be electronically recorded (stored) in memory 2120 of apparatus 100 and/or external server 3000 and/or external server 4000 over time. Apparatus 100 can incorporate a real time clock and status data of apparatus 100 representing a status indicated by the apparatus can be electronically recorded with a time stamp. In another aspect, apparatus 100 can include an I/O interface 2150, e.g., a wireless communication interface for providing bidirectional communication with external CPU equipped computers. In another aspect, status data indicating a status of apparatus 100 can be transmitted to local server 3000 and/or remote server 4000 as shown in FIG. 6 where the status data can be electronically recorded into a database for later retrieval, e.g., for tracking a current or past location of apparatus 100. Server 3000 and server 4000 can have the electrical components as shown in FIG. 18, and in one embodiment can have scaled up versions of such components. Apparatus 100, server 3000, and server 4000, in one embodiment, can be configured to be in network communication with one another and in one particular embodiment can be operative in accordance with the TCP/IP suite of communication protocols. In another aspect, apparatus 100 can be disposed in one or more local area network of a facility in which apparatus 100 is located, e.g., a health care facility wherein the one or more local area network utilizes one or more triangulation algorithms to determine a current coordinate location of apparatus 100. One or more of time stamped status data representing a current status indicated by apparatus 100 and time stamped current coordinate location data of apparatus 100 and can be continually (repeatedly), e.g., at predetermined intervals electronically recorded in memory 2120 and/or transmitted to server 3000 and/or server 4000 for electronically recording into a database defined in a memory 2120 of server 3000 and/or server 4000 in the making of a retrievable record indicating one or more of an indicated status and location of apparatus 100 over time.

In one embodiment a medical apparatus other than apparatus 100 for use with intravenous pole assemblies can incorporate the status indicating features set forth herein.

In another aspect, server 3000 and/or server 4000 can have associated electronic displays 2130 and can be operative to display such status and/or location data transmitted from apparatus 100 over time without being transmitted from apparatus 100. For example, cameras or other external detectors can be utilized for detection of a current status of apparatus 100. Also, with use of triangular technologies, a coordinate location for apparatus 100 can be determined with use of a processing algorithm performed by server 3000 or server 4000, without transmission to apparatus 100 data indicating the coordinate location.

A small sample of systems methods and apparatus that are described herein is as follows:

A1. A method for use in management of a group of intravenous pole assemblies comprising at least first and second intravenous pole assemblies, the method comprising:

providing an apparatus including an arm having disposed thereon a first connector adapted for connecting to an intravenous pole assembly and a second connector adapted for connecting to an intravenous pole assembly, the arm being adapted for providing a spacing between the first connector and the second connector;

connecting the first connector to the first intravenous pole assembly and connecting the second connector to the second intravenous pole assembly, whereupon there is defined by the connecting of the first connector to the first intravenous pole assembly and the connecting of the second connector to the second intravenous pole assembly a group of connected intravenous pole assemblies;

imparting a force to move the group of connected intravenous pole assemblies.

A2. The method of A1, wherein the providing includes providing the apparatus to include at a proximal end of the arm a handle adapted for grasping by an operator.

A3. The method of A1, wherein the providing includes providing the apparatus so that at a proximal end of the arm there is disposed a handle adapted for grasping by an operator, and wherein the imparting includes imparting a force to the handle.

A4. The method of A1, wherein the providing further includes providing the apparatus so that the arm further has disposed thereon a third connector adapted for connecting to an intravenous pole assembly, wherein the method further includes connecting the third connector to a third intravenous pole assembly, whereupon there is defined a group of intravenous pole assemblies comprising the first, second and third intravenous pole assemblies.

A5. The method of A1, wherein the providing includes providing the first connector so that the first connector is adapted for connecting to a pole of an intravenous pole assembly.

A6. The method of A1, wherein the providing includes providing the apparatus to be reconfigurable between compacted and expanded configurations.

A7. The method of A1, wherein the providing includes providing the arm to include a plurality of telescoping members for providing adjustment of a length of the arm.

A8. The method of A1, wherein the providing includes providing the apparatus to be appropriately shaped and balanced as to be capable of being free standed on a horizontal surface in such manner that the arm extends upwardly.

A9. The method of A1, wherein the providing includes providing the arm so that the first connector can be connected to the first intravenous pole assembly by moving the apparatus in a compass direction corresponding to a compass direction of an axis of the arm.

A10. The method of A1, wherein the providing includes providing the first connector so that the first connector is adapted for retaining a pole of an intravenous pole assembly utilizing a spring loaded compression force.

A11. The method of A1, wherein the providing includes providing the first connector so that the first connector is adapted for retaining a pole of an intravenous pole assembly utilizing friction forces.

A12. The method of A1, wherein the providing includes providing the first connector so that the first connector is adapted for retaining a pole of an intravenous pole assembly utilizing magnet forces.

A13. The method of A1, wherein the providing includes providing the first connector so that the first connector is adapted for retaining a pole of an intravenous pole assembly utilizing adhesive forces.

A14. The method of A1, wherein the providing includes providing the first connector to include a roller clamp configuration.

A15. The method of A1, wherein the providing includes providing the first connector to include a resilient pad having a pocket shaped to accommodate a pole of an intravenous pole assembly.

A16. The method of A1, wherein the providing includes providing the first connector to include a lever clasp configuration, the connector adapted to extend 360 degrees about a circumference of a pole of an intravenous pole assembly when in a closed position.

A17. The method of A1 wherein the arm is substantially straight.

A18. The method of A1, wherein the arm is of unitary construction.

A19. The method of A1, wherein the arm comprises one of rigid or semi-rigid material.

A20. The method of A1, wherein the group of intravenous pole assemblies include a third intravenous pole assembly, the method comprising providing a supplementary apparatus having first and second connectors and connecting the supplementary apparatus between the first and third intravenous pole assemblies whereupon there is defined a group of connected intravenous pole assemblies which comprises the first, second, and third intravenous pole assemblies.

A21. The method of A1, wherein the first connector is adapted so that the first connector can be releasably connected and released from an intravenous pole assembly with use of manually generated force.

A22. The method of A1, wherein the second connector is adapted so that the second connector can be releasably connected and released from an intravenous pole assembly with use of manually generated force.

A23. The method of A1, wherein the first connector and second connector are adapted so that the first connector and the second connector can be releasably connected and released from an intravenous pole assembly with use of manually generated force.

A24. The method of A1, wherein the providing includes providing the apparatus to exhibit a color indicating a designated location of the apparatus and wherein the imparting includes imparting a force to move the group of intravenous pole assemblies into the designated location.

A25. The method of A1, wherein the method further includes disposing on the first intravenous pole assembly an adaptation for use in connecting with the first connector of the apparatus.

A26. The method of A25, wherein the adaptation includes microloop and hook fastener material.

A27. The method of A25, wherein the method is devoid of disposing an adaptation on the first intravenous pole assembly for use in connecting with the first connector.

A28. The method of A1, wherein the providing includes providing the apparatus to include a manually actuated status indicator indicating a status of one or more of the apparatus and an intravenous pole assembly and wherein the method includes manually actuating the indicator to change a status indicated by the status indicator.

A29. The method of A28, wherein the providing includes providing the apparatus so that the manually actuated status indicator includes an electronic indicator.

A30. The method of A1, wherein the providing includes providing the apparatus to include a manually actuated status indicator, and wherein the method further includes electronically recording data representing a current status indicted by the status indicator.

A31. The method of A1, wherein the providing includes providing the apparatus to include a manually actuated status indicator, and wherein the method further includes electronically recording, utilizing a server external to the apparatus, data representing the current status indicated by the status indicator.

A32. The method of A1, wherein the method further includes electronically recording data representing a current location of the apparatus.

A33. The method of A1, wherein the method further includes electronically recording, utilizing a server external to the apparatus, data representing a current location of the apparatus.

A34. The method of A1, wherein providing includes providing the apparatus to include a manually actuated status indicator, and wherein the method further includes repeatedly electronically recording time stamped data indicating a current status indicated by the status indicator, and time stamped data indicating a current location of the apparatus.

A35. The method of A1, wherein providing includes providing the apparatus to include a manually actuated status indicator, and wherein the method further includes, utilizing a server external to the apparatus, repeatedly electronically recording time stamped data indicating a current status indicated by the status indicator, and time stamped data indicating a current location of the apparatus.

A36. The method of A1, wherein the first connector and the second connector are adapted so that each of the first connector and the second connector can be connected to a pole of an intravenous pole assembly with use of a single direction manually imparted push force manually imparted to the apparatus, and wherein the first connector and the second connector are adapted so that each of the first connector and the second connector can be released to a pole of an intravenous pole assembly with use of a single direction manually imparted pull force manually imparted to the apparatus.

B1. A method for use in management of a group of intravenous pole assemblies comprising at least first and second intravenous pole assemblies, the method comprising:

providing an apparatus including an arm having disposed thereon a first connector adapted for connecting to a pole and a second connector adapted for connecting to a pole, the arm being adapted for providing a spacing between the first connector and the second connector;

connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;

imparting a force to move the group of connected intravenous pole assemblies.

B2. The method of B1, wherein the providing includes providing the apparatus to include at a proximal end of the arm a handle adapted for grasping by an operator.

B3. The method of B1, wherein the providing includes providing the apparatus so that at a proximal end of the arm there is disposed a handle adapted for grasping by an operator, and wherein the imparting includes imparting a force to the handle.

B4. The method of B1, wherein the providing further includes providing the apparatus so that the arm further has disposed thereon a third connector adapted for connecting to an intravenous pole assembly, wherein the method further includes connecting the third connector to a third intravenous pole assembly, whereupon there is defined a group of intravenous pole assemblies comprising the first, second and third intravenous pole assemblies.

B5. The method of B1, wherein the providing includes providing the first connector so that the first connector is adapted for connecting to a vertically extending pole of an intravenous pole assembly.

B6. The method of B1, wherein the providing includes providing the apparatus to be reconfigurable between compacted and expanded configurations.

B7. The method of B1, wherein the providing includes providing the arm to include a plurality of telescoping members for providing adjustment of a length of the arm.

B8. The method of B1, wherein the providing includes providing the apparatus to be appropriately shaped and balanced as to be capable of being free standed on a horizontal surface in such manner that the arm extends upwardly.

B9. The method of B1, wherein the providing includes providing the arm so that the first connector can be connected to the first intravenous pole assembly by moving the apparatus in a compass direction corresponding to a compass direction of an axis of the arm.

B10. The method of B1, wherein the providing includes providing the first connector so that the first connector is adapted for retaining a pole of an intravenous pole assembly utilizing a spring loaded compression force.

B11. The method of B1, wherein the providing includes providing the first connector so that the first connector is adapted for retaining a pole of an intravenous pole assembly utilizing friction forces.

B12. The method of B1, wherein the providing includes providing the first connector so that the first connector is adapted for retaining a pole of an intravenous pole assembly utilizing magnet forces.

B13. The method of B1, wherein the providing includes providing the first connector so that the first connector is adapted for retaining a pole of an intravenous pole assembly utilizing adhesive forces.

B14. The method of B1, wherein the providing includes providing the first connector to include a roller clamp configuration.

B15. The method of B1, wherein the providing includes providing the first connector to include a resilient pad having a pocket shaped to accommodate a pole of an intravenous pole assembly.

B16. The method of B1, wherein the providing includes providing the first connector to include a lever clasp configuration, the connector adapted to extend 360 degrees about a circumference of a pole of an intravenous pole assembly when in a closed position.

B17. The method of B1 wherein the arm is substantially straight.

B18. The method of B1, wherein the arm is of unitary construction.

B19. The method of B1, wherein the arm comprises one of rigid or semi-rigid material.

B20. The method of B1, wherein the group of intravenous pole assemblies include a third intravenous pole assembly, the method comprising providing a supplementary apparatus having first and second connectors and connecting the supplementary apparatus between the first and third intravenous pole assemblies whereupon there is defined a group of connected intravenous pole assemblies which comprises the first, second, and third intravenous pole assemblies.

B21. The method of B1, wherein the first connector is adapted so that the first connector can be releasably connected and released from an intravenous pole assembly with use of manually generated force.

B22. The method of B1, wherein the second connector is adapted so that the second connector can be releasably connected and released from an intravenous pole assembly with use of manually generated force.

B23. The method of B1, wherein the first connector and second connector are adapted so that the first connector and the second connector can be releasably connected and released from an intravenous pole assembly with use of manually generated force.

B24. The method of B1, wherein the providing includes providing the apparatus to exhibit a color indicating a designated location of the apparatus and wherein the imparting includes imparting a force to move the group of intravenous pole assemblies into the designated location.

B25. The method of B1, wherein the method further includes disposing on the first intravenous pole assembly an adaptation for use in connecting with the first connector of the apparatus.

B26. The method of B25, wherein the adaptation includes microloop and hook fastener material.

B27. The method of B25, wherein the method is devoid of disposing an adaptation on the first intravenous pole assembly for use in connecting with the first connector.

B28. The method of B1, wherein the providing includes providing the apparatus to include a manually actuated status indicator indicating a status of one or more of the apparatus and an intravenous pole assembly and wherein the method includes manually actuating the status indicator to change a status indicated by the indicator.

B29. The method of B28, wherein the providing includes providing the apparatus so that the manually actuated status indicator includes an electronic indicator.

B30. The method of B1, wherein the providing includes providing the apparatus to include a manually actuated status indicator, and wherein the method further includes electronically recording data representing a current status indicted by the status indicator.

B31. The method of B1, wherein the providing includes providing the apparatus to include a manually actuated status indicator, and wherein the method further includes electronically recording, utilizing a server external to the apparatus, data representing the current status indicated by the indicator.

B32. The method of B1, wherein the method further includes electronically recording data representing a current location of the apparatus.

B33. The method of B1, wherein the method further includes electronically recording, utilizing a server external to the apparatus, data representing a current location of the apparatus.

B34. The method of B1, wherein providing includes providing the apparatus to include a manually actuated status indicator, and wherein the method further includes repeatedly electronically recording time stamped data indicating a current status indicated by the status indicator, and time stamped data indicating a current location of the apparatus.

B35. The method of B1, wherein providing includes providing the apparatus to include a manually actuated status indicator, and wherein the method further includes, utilizing a server external to the apparatus, repeatedly electronically recording time stamped data indicating a current status indicated by the status indicator, and time stamped data indicating a current location of the apparatus.

B36. The method of B1, wherein the first connector and the second connector are adapted so that each of the first connector and the second connector can be connected to a pole of an intravenous pole assembly with use of a single direction manually imparted push force manually imparted to the apparatus, and wherein the first connector and the second connector are adapted so that each of the first connector and the second connector can be released to a pole of an intravenous pole assembly with use of a single direction manually imparted pull force manually imparted to the apparatus.

C1. A method for transporting a plurality of medical intravenous pole assemblies within a health care facility in which there are included first and second medical intravenous pole assemblies, each of the first and second medical intravenous pole assemblies having a base including a plurality of wheels and a vertically extending pole, the method comprising the steps of:

physically associating at least the first and second medical intravenous pole assemblies to define a group of medical intravenous pole assemblies; and pushing the group of medical intravenous pole assemblies from a first location within the facility to a second location within the facility.

C2. The method of C1, wherein the physically associating includes connecting the first and second medical intravenous poles utilizing an apparatus having an elongated section extending between respective poles of the first and second medical intravenous pole assemblies.

C3. The method of C1, wherein the facility further includes a third medical intravenous pole assembly; and wherein the physically associating includes physically associating the first, second, and third medical intravenous pole assemblies.

D1. A system comprising;

a first medical intravenous pole assembly including a wheeled base and a vertically extended pole;

a second medical intravenous pole assembly including a wheeled base and a vertically extending pole;

an apparatus connecting the first medical intravenous pole assembly and the second medical intravenous pole assembly, the apparatus including an arm extending between the first medical intravenous pole assembly and the second medical intravenous pole assembly;

the arm having a first connector disposed at a first location of the arm for detachable connection to the first medical intravenous pole assembly;

the arm having a second connector disposed at a second location of the arm for detachable connection to the second medical intravenous pole assembly, the second location being spaced apart from the first location;

wherein the arm is of rigid or semi-rigid construction for providing spacing between a component of the first medical intravenous pole assembly and a component of the second medical intravenous pole assembly.

D2. The system of D1, wherein the system comprises a third medical intravenous pole assembly, and wherein the arm further comprises a third connector disposed at a third position of the arm, the first, second, and third positions being spaced apart positions.

D3. The system of D1, wherein the system comprises a third medical intravenous pole assembly, and wherein the arm includes a third connector disposed at a third position on the arm and being detachably connected to the third medical intravenous pole assembly, wherein the arm includes a first segment extending between the first position and the second position, and a second segment extending between the second position and the third position, and wherein the apparatus includes a collapsed configuration in which a length of the arm is substantially determined by a length of the first segment.

E1. An apparatus comprising:

an arm;

a first connector disposed at a first location on the arm;

a second connector disposed at a second location on the arm, the second position being spaced apart from the first position;

wherein the first connector is adapted for connection to a first vertically extending pole;

wherein the second connector is adapted for connection to a second vertically extending pole;

wherein the arm is constructed so that there is defined a spacing between the first position and the second position; and wherein the apparatus is characterized by one or more of (a) the apparatus includes a handle specially adapted for grasping by an operator extending from the arm; (b) the arm is adapted so a length of the arm can be adjusted; and (c) the apparatus is adapted so that the apparatus can be freely standed on a horizontal surface in such manner that the arm extends upwardly.

E2. The apparatus of E1, wherein the apparatus further includes a handle extending from the arm.

E3. The apparatus of E1, wherein the apparatus includes a third connector disposed at a third position of the arm, the first, second, and third positions being spaced apart positions the arm including a first segment extending between the first connector and the second connector, and a second segment extending between the second connector and the third connector.

E4. The apparatus of E3, wherein the apparatus is adapted to be reconfigurable between a first state in which a length of the arm is substantially a sum of the lengths of the first and second segments and a second state in which a length of arm is substantially a length of the first segment.

F1. An apparatus comprising:

an arm;

a first connector disposed at a first location on the arm;

a second connector disposed at a second location on the arm, the second position being spaced apart from the first position;

wherein the first connector is adapted for connection to a first vertically extending pole;

wherein the second connector is adapted for connection to a second vertically extending pole;

wherein the arm is constructed so that there is defined a spacing between the first position and the second position.

G1. A medical apparatus comprising:

a visually observable status indicator, wherein the visually observable status indicator is configured to be manually actuated.

G2. The medical apparatus of G1, wherein the apparatus includes a first connector adapting the apparatus for connection to a first intravenous pole assembly and a second connector adapting the apparatus for connection to a second intravenous pole assembly.

G3. The medical apparatus of G1, wherein the apparatus includes one or more surfaces defining a first surface location and a second surface location, the apparatus having a first visible color at the first surface location and a second visible color at the second surface location, wherein the apparatus includes a structure moveable between a first position at which the structure covers the first surface location and a second position at which the structure covers the second surface location.

G4. The medical apparatus of G1, wherein the apparatus is adapted so that data indicating a current status of the apparatus is electronically recorded over time in a memory of one or more of the apparatus and a server external to the apparatus.

G5. The apparatus of G1, wherein the apparatus is adapted to at least one of electronically store and transmit data indicating one or more of (a) a status indicated by the status indicator; and (b) a current location of the apparatus.

H1. A method for use in transport of a group of intravenous pole assemblies comprising at least first and second intravenous pole assemblies, the method comprising:

providing an apparatus including an arm having disposed thereon a first connector adapted for connecting to an intravenous pole assembly and a second connector adapted for connecting to an intravenous pole assembly, the arm being adapted for providing a spacing between the first connector and the second connector;

connecting the first connector to the first intravenous pole assembly and connecting the second connector to the second intravenous pole assembly, whereupon there is defined by the connecting of the first connector to the first intravenous pole assembly and the connecting of the second connector to the second intravenous pole assembly a group of connected intravenous pole assemblies;

imparting a force to move the group of connected intravenous pole assemblies.

11. A method for use in transport of a group of intravenous pole assemblies comprising at least first and second intravenous pole assemblies, the method comprising:

providing an apparatus including an arm having disposed thereon a first connector adapted for connecting to a pole and a second connector adapted for connecting to a pole, the arm being adapted for providing a spacing between the first connector and the second connector;

connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;

imparting a force to move the group of connected intravenous pole assemblies.

While the present application has been described with reference to a number of specific embodiments, it will be understood that the true spirit and scope of the application should be determined only with respect to claims that can be supported by the present specification. Further, while in numerous cases herein wherein systems and apparatuses and methods are described as having a certain number of elements it will be understood that such systems, apparatuses and methods can be practiced with fewer than or more than the mentioned certain number of elements. Also, while a number of particular embodiments have been set forth, it will be understood that features and aspects that have been described with reference to each particular embodiment can be used with each remaining particularly set forth embodiment.

We claim:

1. A method for use in management of a group of intravenous pole assemblies comprising at least first and second intravenous pole assemblies, the method comprising:

providing an apparatus including an arm having disposed thereon a first connector adapted for connecting to a pole and a second connector adapted for connecting to a pole, the arm being adapted for providing a spacing between the first connector and the second connector;

connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;

imparting a force to move the group of connected intravenous pole assemblies;

wherein the first connector and the second connector are adapted so that each of the first connector and the second connector can be connected to a pole of an intravenous pole assembly using a single direction manually imparted push force manually imparted to the apparatus, and wherein the first connector and the second connector are adapted so that each of the first connector and the second connector can be released from a pole of an intravenous pole assembly using a single direction manually imparted pull force manually imparted to the apparatus, and wherein the first connector is adapted so that when the first connector is connected to the pole of the first intravenous pole assembly the pole of the first intravenous pole assembly can be rotated about an axis of the pole of the first intravenous pole assembly with an orientation of the first connector remaining constant, wherein the providing includes providing the apparatus so that at a proximal end of the arm there is disposed a handle adapted for grasping by an operator, wherein the handle extends away from the proximal end of the arm, wherein the first connector is disposed more proximate the proximal end than the second connector, wherein a distance between the handle and the second connector is greater than a distance between the first connector and the second connector, and wherein the imparting includes imparting a force to the handle.

2. The method of claim 1, wherein the providing further includes providing the apparatus so that the arm further has disposed thereon a third connector adapted for connecting to an intravenous pole assembly, wherein the method further includes connecting the third connector to a third intravenous pole assembly, whereupon there is defined a group of intravenous pole assemblies comprising the first, second and third intravenous pole assemblies.

3. The method of claim 1, wherein the providing includes providing the apparatus to be reconfigurable between compacted and expanded configurations.

4. The method of claim 1, wherein the providing includes providing the apparatus to be shaped and balanced as to be capable of being free standed on a horizontal surface in such manner that the arm extends upwardly.

5. The method of claim 1, wherein the providing includes providing the arm so that the first connector can be connected to the first intravenous pole assembly by moving the apparatus in a direction corresponding to a direction of an axis of the arm.

6. The method of claim 1, wherein the providing includes providing the first connector so that the first connector is adapted for retaining a pole of an intravenous pole assembly utilizing a spring loaded compression force.

7. The method of claim 1, wherein the providing includes providing the first connector to include a roller clamp configuration, wherein the first connector includes first and second rollers adapted for contact with said pole of the first intravenous pole assembly, wherein members supporting the first and second rollers are adapted to move from their unstressed state to accommodate a connection, and wherein the members supporting the first and second rollers are adapted to transfer a spring-loaded compression force to the rollers when a connection is made.

8. The method of claim 1, wherein the providing includes providing the first connector to include a resilient pad having a pocket shaped to accommodate a pole of an intravenous pole assembly.

9. The method of claim 1, wherein the providing includes providing the apparatus to exhibit a color indicating a designated location of the apparatus and wherein the imparting includes imparting a force to move the group of intravenous pole assemblies into the designated location.

10. The method of claim 1, wherein the providing includes providing the apparatus to include a manually actuated status indicator indicating a status of one or more of the apparatus and an intravenous pole assembly and wherein the method includes manually actuating the status indicator to change a status indicated by the indicator.

11. The method of claim 1, wherein the providing includes providing the apparatus to include a manually actuated status indicator, and wherein the method further includes electronically recording data representing a current status indicted by the status indicator.

12. The method of claim 1, wherein providing includes providing the apparatus to include a manually actuated status indicator, and wherein the method further includes repeatedly electronically recording time stamped data indicating a current status indicated by the status indicator, and time stamped data indicating a current location of the apparatus.

13. The method of claim 1, wherein, the imparting a force comprises imparting a pushing force to move the group of connected intravenous pole assemblies.

14. The method of claim 1, wherein the first connector is adapted so that when the first connector is connected to the pole of the first intravenous pole assembly, the first connector extends less than 360 degrees about the pole of the first intravenous pole assembly.

15. The method of claim 1, wherein the method is devoid of disposing a structural adaptation on the first intravenous pole assembly for use in connecting with the first connector.

16. The method of claim 1, wherein the first connector defines a connection axis along which the first connector can be moved to connect and disconnect the first connector from a pole of the first intravenous pole assembly using a single direction manual push force and single direction manual pull force, respectively, the connection axis extending generally transverse to a longitudinal axis of the arm.

17. The method of claim 1, wherein the imparting a force comprises imparting a pushing force to move the group of connected intravenous pole assemblies, and wherein the pushing force is imparted to the handle, and wherein the handle is intersected by a longitudinal axis of the arm.

18. The method of claim 1, wherein the handle is adapted for grasping by including a feature selected from the group consisting of (a) a closed perimeter shape, (b) a semi-closed perimeter shape, (c) a curved configuration, and (d) a resilient material construction.

19. A method for use in management of a group of intravenous pole assemblies comprising at least first and second intravenous pole assemblies, the method comprising:
providing an apparatus including an arm having disposed thereon a first connector adapted for connecting to a pole and a second connector adapted for connecting to a pole, the arm being adapted for providing a spacing between the first connector and the second connector;
connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;
imparting a force to move the group of connected intravenous pole assemblies;
wherein the method includes using a second apparatus having an arm and a plurality of connectors to connect a third intravenous pole assembly to the second intravenous pole assembly, whereupon there is defined a group of intravenous pole assemblies comprising the first, second and third intravenous pole assemblies, and moving the first intravenous pole assembly and the third intravenous pole assembly between different relative orientations while moving the group of intravenous pole assemblies comprising the first, second and third intravenous pole assemblies through a narrow width space or around an obstacle.

20. A method for use in management of a group of intravenous pole assemblies comprising at least first and second intravenous pole assemblies, the method comprising:
providing an apparatus including an arm having disposed thereon a first connector adapted for connecting to a pole and a second connector adapted for connecting to a pole, the arm being adapted for providing a spacing between the first connector and the second connector;
connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;
imparting a force to move the group of connected intravenous pole assemblies;
wherein the first connector and the second connector are adapted so that each of the first connector and the second connector can be connected to a pole of an intravenous pole assembly using a single direction manually imparted push force manually imparted to the apparatus, and wherein the first connector and the second connector are adapted so that each of the first connector and the second connector can be released from a pole of an intravenous pole assembly using a single direction manually imparted pull force manually imparted to the apparatus, wherein the first connector is adapted so that when the first connector is connected to the pole of the first intravenous pole assembly, the first connector extends less than 360 degrees about the pole of the first intravenous pole assembly, wherein at a proximal end of the arm there is disposed a handle adapted for grasping by an operator, wherein the handle extends away from the proximal end of the arm, wherein the first connector is disposed more proximate the proximal end than the second connector, wherein a distance between the handle and the second connector is greater than a distance between the first connector and the second connector, and wherein the imparting includes imparting a force to the handle.

21. The method of claim 20, wherein the providing includes providing the apparatus to be shaped and balanced as to be capable of being free standed on a horizontal surface in such manner that the arm extends upwardly.

22. The method of claim 20, wherein the first connector is adapted so that when the first connector is connected to the pole of the first intravenous pole assembly the pole of the first intravenous pole assembly can be rotated about an axis of the pole of the first intravenous pole assembly with an orientation of the first connector remaining constant.

23. A method for use in management of a group of intravenous pole assemblies comprising at least first and second intravenous pole assemblies, the method comprising:
providing an apparatus including an arm having disposed thereon a first connector adapted for connecting to a pole and a second connector adapted for connecting to a pole, the arm being adapted for providing a spacing between the first connector and the second connector;
connecting the first connector to a pole of the first intravenous pole assembly and connecting the second connector to a pole of the second intravenous pole assembly, whereupon there is defined by the connecting of the first connector to the pole of the first intravenous pole assembly and the connecting of the second connector to the pole of the second intravenous pole assembly a group of connected intravenous pole assemblies;

imparting a force to move the group of connected intravenous pole assemblies;

wherein the providing includes providing the first connector to include a roller clamp configuration, wherein the first connector includes first and second rollers adapted for contact with said pole of the first intravenous pole assembly, wherein members supporting the first and second rollers are adapted to move from their unstressed state to accommodate a connection, and wherein the members supporting the first and second rollers are adapted to transfer a spring-loaded compression force to the rollers when a connection is made, wherein the providing includes providing the apparatus so that at a proximal end of the arm there is disposed a handle adapted for grasping by an operator, wherein the handle extends away from the proximal end of the arm, wherein the first connector is disposed more proximate the proximal end than the second connector, wherein a distance between the handle and the second connector is greater than a distance between the first connector and the second connector, and wherein the imparting includes imparting a force to the handle.

24. The method of claim 23, wherein the first connector and second connector are adapted so that the first connector and the second connector can be releasably connected and released from an intravenous pole assembly with use of manually generated force.

25. The method of claim 23, wherein the first connector and the second connector are adapted so that each of the first connector and the second connector can be connected to a pole of an intravenous pole assembly using a single direction manually imparted push force manually imparted to the apparatus, and wherein the first connector and the second connector are adapted so that each of the first connector and the second connector can be released from a pole of an intravenous pole assembly using a single direction manually imparted pull force manually imparted to the apparatus.

26. The method of claim 23, wherein the first connector and the second connector are adapted so that each of the first connector and the second connector can be connected to a pole of an intravenous pole assembly using a single direction manually imparted push force manually imparted to the apparatus, and wherein the first connector and the second connector are adapted so that each of the first connector and the second connector can be released from a pole of an intravenous pole assembly using a single direction manually imparted pull force manually imparted to the apparatus, and wherein the first connector is adapted so that when the first connector is connected to the pole of the first intravenous pole assembly the pole of the first intravenous pole assembly can be rotated about an axis of the pole of the first intravenous pole assembly with an orientation of the first connector remaining constant, wherein the first connector is adapted so that when the first connector is connected to the pole of the first intravenous pole assembly, the first connector extends less than 360 degrees about the pole of the first intravenous pole assembly.

27. The method of claim 23, wherein the providing includes providing the apparatus to be shaped and balanced as to be capable of being free standed on a horizontal surface in such manner that the arm extends upwardly.

\* \* \* \* \*